(12) United States Patent
Hoshino et al.

(10) Patent No.: US 9,187,690 B2
(45) Date of Patent: *Nov. 17, 2015

(54) RARE EARTH METAL COMPLEX HAVING PHENANTHROLINE COMPOUND AS LIGAND

(75) Inventors: Mikio Hoshino, Tsurugashima (JP); Toshisada Yano, Kobe (JP); Yasukazu Yamanaka, Inashiki-gun (JP)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/004,516

(22) PCT Filed: Mar. 12, 2012

(86) PCT No.: PCT/JP2012/001707
§ 371 (c)(1),
(2), (4) Date: Nov. 18, 2013

(87) PCT Pub. No.: WO2012/124310
PCT Pub. Date: Sep. 20, 2012

(65) Prior Publication Data
US 2014/0058073 A1 Feb. 27, 2014

Related U.S. Application Data

(60) Provisional application No. 61/451,904, filed on Mar. 11, 2011.

(51) Int. Cl.
*C07D 471/04* (2006.01)
*C07D 471/22* (2006.01)
*C09K 11/06* (2006.01)

(52) U.S. Cl.
CPC ............. *C09K 11/06* (2013.01); *C07D 471/22* (2013.01)

(58) Field of Classification Search
CPC ........................... C07D 471/04; C07D 455/04
USPC .................. 525/363, 391, 396, 401, 403, 423
See application file for complete search history.

(56) References Cited

U.S. PATENT DOCUMENTS

| | | | |
|---|---|---|---|
| 4,283,382 A * | 8/1981 | Frank et al. .................... | 436/533 |
| 5,424,381 A | 6/1995 | Yamamoto et al. | |
| 7,679,082 B2 * | 3/2010 | Ling et al. ........................ | 257/40 |
| 2006/0097227 A1 | 5/2006 | Okajima et al. | |
| 2009/0218940 A1 | 9/2009 | Okajima et al. | |
| 2012/0238748 A1 | 9/2012 | Hoshino et al. | |

FOREIGN PATENT DOCUMENTS

| | | |
|---|---|---|
| JP | 6-279572 A | 10/1994 |
| WO | 2004 026870 | 4/2004 |
| WO | 2011 030566 | 3/2011 |
| WO | WO-2011/030566 * | 3/2011 |

OTHER PUBLICATIONS

International Search Report Issued May 31, 2012 in PCT/JP12/01707 Filed Mar. 12, 2012.
International Search Report issued Nov. 8, 2010 in PCT/JP2010/005588.
Jeremy K. Klosterman, et al., "Synthesis of aryl-substituted 2-pyridyl-1,10-phenanthrolines; a series of oriented terpyridine analogues", Organic & Biomolecular Chemistry, vol. 6, XP2606398A, 2008, pp. 2755-2764.
Jon C. Loren, et al., "Synthesis and Fluorescence Properties of Manisyl-Substituted Terpyridine, Bipyridine, and Phenanthroline", Angewante Chemie International Edition, vol. 40, No. 4, XP2605399A, 2001, pp. 754-757.
Theodora W. Greene, et al., "Protective Groups in Organic Synthesis", John Wiley & Sons, Inc., 1991, pp. 1-473 with cover pages.
"Dictionary of Organic Compounds" Chapman and Hall, 6th edition, vol. 5, 1996, pp. 5167-5168 with cover page.
Munio Kotake, "Dai-Yuki Kagaku", Fukusokanshiki Kagobutu III, Asakura Publishing Co., Ltd., Apr. 1964, pp. 356-363 with cover page and English translation.
Shojiro Ogawa, et al., "Preparation of a Conjugated Tautomer of 1,14:7,8-Diethenotetrapyrido- [2,1,6-de: 2',1',6'-gh: 2",1",6"-kl: 2''',1''',6'''—na] [1,3,5,8,10,12] hexa-azacyclotetradecine and its Metal Derivatives" J.C.S. Perkin I, 1974, pp. 976-978.

* cited by examiner

*Primary Examiner* — Michael G Hartley
*Assistant Examiner* — Jagadishwar Samala
(74) *Attorney, Agent, or Firm* — Oblon, McClelland, Maier & Neustadt, L.L.P.

(57) ABSTRACT

The present invention provides a rare earth metal complex represented by the following formula (I).

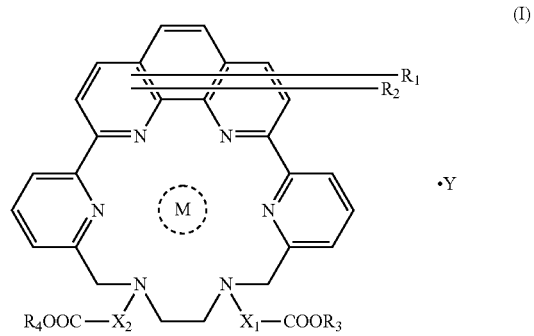

20 Claims, 2 Drawing Sheets

RARE EARTH METAL COMPLEX HAVING PHENANTHROLINE COMPOUND AS LIGAND

CROSS REFERENCE TO RELATED APPLICATION

This application is a 371 of PCT/JP2012/001707, filed on Mar. 12, 2012, and claims the benefit of U.S. provisional application No. 61/451,904, filed on Mar. 11, 2011.

TECHNICAL FIELD

The present invention relates to a rare earth metal complex having a phenanthroline compound as a ligand.

BACKGROUND ART

Recently, functions of metal complexes such as photoreactive functions, electron-transfer functions, and physiologically active functions have been attracting attention, and a number of researches are being conducted by utilizing such functions. Further, researches on ligands that bind to metal elements have also been conducted. As a representative ligand, a unidentate ligand such as ammonia, pyridine, and a cyanide ion, a bidentate ligand such as ethylenediamine, bipyridine, and glycinato, and a multidentate ligand having a coordination number of three or more such as ethylenediaminete-traacetic acid are known.

Bipyridine, which is a representative bidentate ligand, has a chelate ligand structure and a function of coordinating with a metal element. However, owing to poor solubility of bipyridine metal complexes in organic solvents, there has been a problem that the utility range of such a complex is extremely limited.

Patent Literature 1 discloses a compound in which a long chain alkyl group such as a hexyl group, pentyl group, octyl group or decyl group is introduced into a polypyridine.

Although Patent Literature 2 discloses a phenanthroline compound in which an aromatic cyclic group has been substituted, there is no description of a metal complex having the phenanthroline compound as a ligand thereof. Examples of ligands of the metal complex described in this document include phenylpyridine, quinoline and benzimidazole, and these compounds have completely different structures from the ligands of the rare earth metal complexes of the present invention.

Non-Patent Literature 1 discloses a ligand that is a 2-pyridylphenanthroline compound, and describes a ruthenium complex having this ligand. In addition, although Non-Patent Literature 2 discloses phenanthroline compounds having a 2-pyridyl group or phenyl group, the structures of both of these compounds are completely different from the ligands of the rare earth metal complexes of the present invention.

CITATION LIST

Patent Literature

[PTL 1] Patent Publication JP-A-H6-279572
[PTL 2] WO 2004/026870

Non Patent Literature

[NPL 1] Organic & Biomolecular Chemistry, 2008, vol. 6, no. 15, pages 2755-2764

[NPL 2] Angewante Chemie International Edition, 2001, vol. 40, no. 4, pages 754-757

SUMMARY OF INVENTION

Technical Problem

Numerous studies have been conducted on complexes having a rare earth metal for the central metal (rare earth metal complexes) based on their superiority as light-emitting probes for biological samples in terms of their long emission life, high emission yield, resistance to quenching by oxygen and the like. However, a rare earth metal complex had the problem of light emission becoming extremely weak when a water molecule coordinates thereto.

In addition, with respect to fluorescence detection using a rare earth metal complex, since the absorption wavelength of a ligand is a short, it is necessary to use an expensive nitrogen laser for the light source, while in the case of a xenon flash lamp used as a general-purpose pulsed light source, there was the problem of being unable to efficiently excite the rare earth metal complex due to the poor emission efficiency of the ultraviolet portion required for excitation of the complex.

Thus, creation of an improved light-emitting substance that is further improved compared to an existing rare earth metal complex is demanded.

Solution to Problem

In order to solve the aforementioned problems, the present inventors conducted intensive studies. As a result, they have found a novel rare earth metal complex having, for a ligand thereof, a phenanthroline compound having a ring moiety in a molecule as a structural characteristic, thereby completing the present invention.

That is, the present inventions are as follows.

[1] A rare earth metal complex represented by the following formula (I):

Formula (I):

[Chem. 1]

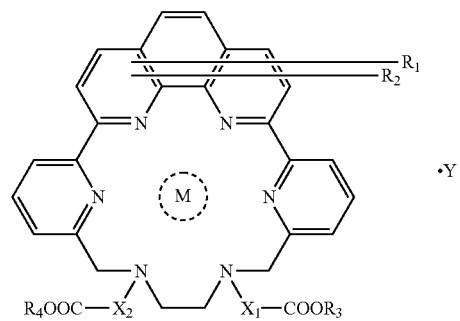

(wherein,
M represents a divalent or trivalent rare earth metal ion,
$R_1$ and $R_2$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycyloalkylsulfinyl group, (27) a $C_{3-8}$ cycloalkyl-sulfonyl group, (28) a carboxyl group, (29) a $C_{1-6}$ alkyloxycarbonyl group, (30) a $C_{6-14}$ aryl group, (31) a $C_{7-20}$ aralkyl group or (32) a carboxyl ion, $R_3$ and $R_4$ are the same as or different from each other and each independently represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, (7) a $C_{7-20}$ aralkyl group, or (8) a negative charge, $X_1$ and $X_2$ are the same as or different from each other and each independently represents the following structure:

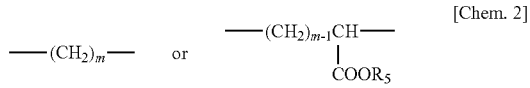

[Chem. 2]

(wherein, m represents an integer of 1 to 6, and $R_5$ represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, (7) a $C_{7-20}$ aralkyl group, or (8) a negative charge), and Y represents an anion or is not present).

[2] The rare earth metal complex described in [1] above, wherein each of $R_3$ and $R_4$ independently represents a hydrogen atom or a negative charge.

[3] The rare earth metal complex described in [1] above, wherein the rare earth metal is europium.

[4] A fluorescent labeling agent containing the rare earth metal complex described in [1] above.

Advantageous Effects of Invention

Use of the rare earth metal complex of the present invention made it possible to measure fluorescence with a light source of a wavelength range extending from the near ultraviolet region to the visible region. As a result of solving the existing problems, the rare earth metal complex of the present invention has made it possible to obtain a fluorescent labeling agent that takes advantage of the inherent emission property of rare earth metal complexes.

DESCRIPTION OF EMBODIMENTS

Figure 1:
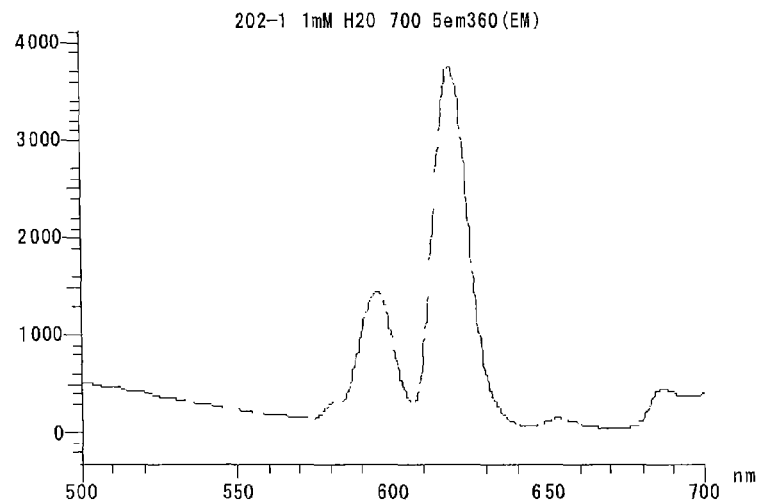
FIG. 1 shows the result of measuring the fluorescence spectrum of complex 1 at an excitation wavelength of 360 nm.

The rare earth metal complex of the present invention is a complex represented by the following formula (I), and a metal complex having a rare earth metal for the central metal and having a phenanthroline compound as a ligand.

Formula (I):

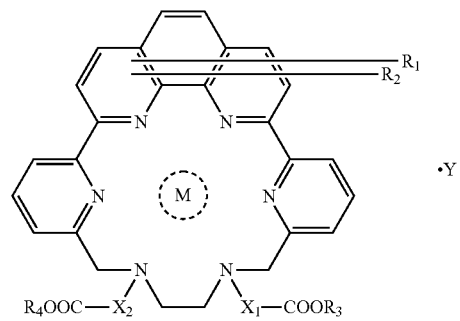

[Chem. 3]

In the above formula (I),

M represents a divalent or trivalent rare earth metal ion, $R_1$ and $R_2$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycyloalkylsulfinyl group, (27) a $C_{3-8}$ cycloalkyl-sulfonyl group, (28) a carboxyl group, (29) a $C_{1-6}$ alkyloxycarbonyl group, (30) a $C_{6-14}$ aryl group, (31) a $C_{7-20}$ aralkyl group or (32) a carboxyl ion, $R_3$ and $R_4$ are the same as or different from each other and each independently represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, (7) a $C_{7-20}$ aralkyl group, or (8) a negative charge, $X_1$ and $X_2$ are the same as or different from each other and each independently represents the following structure:

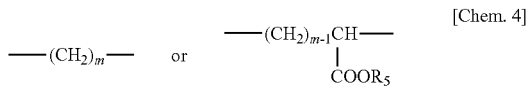

[Chem. 4]

(wherein, m represents an integer of 1 to 6, and $R_5$ represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, (7) a $C_{7-20}$ aralkyl group, or (8) a negative charge), and Y represents an anion or is not present.

The terms used in the present specification will be described.

The term "halogen atom" refers to a fluorine atom, a chlorine atom, a bromine atom, an iodine atom, and the like. Among them, a chlorine atom, a bromine atom, and an iodine atom are preferable, and a chlorine atom and a bromine atom are more preferable.

The term "$C_{1-6}$ alkyl group" refers to a linear-chain or branched-chain aliphatic hydrocarbon group containing 1 to 6 carbons. Specific examples thereof include a methyl group, an ethyl group, a propyl group, an isopropyl group, a butyl group, a sec-butyl group, a tert-butyl group, a pentyl group, an isopentyl group, and a hexyl group. Among them, a methyl group, an ethyl group, a propyl group, and a tert-butyl group are preferable, and a methyl group and an ethyl group are more preferable.

The term "$C_{3-8}$ cycloalkyl group" refers to a cyclic aliphatic hydrocarbon group containing 3 to 8 carbons. Specific examples thereof include a cyclopropyl group, a cyclobutyl group, a cyclopentyl group, a cyclohexyl group, and a cyclooctyl group. Among them, a cyclopropyl group, a cyclobutyl group, a cyclopentyl group, and a cyclohexyl group are preferable, and a cyclopropyl group and a cyclobutyl group are more preferable.

The term "$C_{2-6}$ alkenyl group" refers to a linear-chain or branched-chain aliphatic hydrocarbon group containing 2 to 6 carbons and having one or two double bonds. Specific examples thereof include an ethenyl group, a 2-propenyl group, a 1-propenyl group, a 1-methyl vinyl group, a 1-butenyl group, a 2-butenyl group, a 3-butenyl group, a 1,3-pentadienyl group, a 1,4-hexadienyl group, a 5-pentenyl group, and a 6-hexenyl group. Among them, an ethenyl group, a 2-propenyl group, a 1-propenyl group, and a 1-methyl vinyl group are preferable, and an ethenyl group and a 1-propenyl group are more preferable.

The term "$C_{2-6}$ alkynyl group" refers to a linear-chain or a branched-chain aliphatic hydrocarbon group containing 2 to 6 carbons and having one or two triple bonds. Specific examples thereof include an ethynyl group, a 1-propynyl group, a 2-propynyl group, a butynyl group, a 1,3-pentanediynyl group, a 1,4-hexadiynyl group, a pentynyl group, and a hexynyl group. Among them, an ethynyl group, a 1-propynyl group, a 2-propynyl group, and a butynyl group are preferable, and an ethynyl group and a 2-propynyl group are more preferable.

The term "$C_{1-6}$ alkoxy group" refers to a group with an oxygen atom to which a $C_{1-6}$ alkyl group is bonded. Specific examples thereof include a methoxy group, an ethoxy group, a propoxy group, an isopropoxy group, a butoxy group, a sec-butoxy group, a tert-butoxy group, a pentyloxy group, an isopentyloxy group, and a hexyloxy group. Among them, a methoxy group, an ethoxy group, a propoxy group, and a tert-butoxy group are preferable, and a methoxy group and an ethoxy group are more preferable.

The term "$C_{3-8}$ cycloalkoxy group" refers to a group with an oxygen atom to which a $C_{3-8}$ cycloalkyl group is bonded. Specific examples thereof include a cyclopropoxy group, a cyclobutoxy group, a cyclopentyloxy group, a cyclohexyloxy group, and a cyclooctyloxy group. Among them, a cyclopropoxy group, a cyclobutoxy group, a cyclopentyloxy group, and a cyclohexyloxy group are preferable, and a cyclopropoxy group and a cyclobutoxy group are more preferable.

The term "$C_{2-6}$ alkenyloxy group" refers to a group with an oxygen atom to which a $C_{2-6}$ alkenyl group is bonded. Specific examples thereof include an ethenyloxy group, a 2-propenyloxy group, a 1-propenyloxy group, a 1-methylvinyloxy group, a 1-butenyloxy group, a 2-butenyloxy group, a 3-butenyloxy group, a 1,3-pentadienyloxy group, a 1,4-hexadienyloxy group, a 5-pentenyloxy group, and a 6-hexenyloxy group. Among them, an ethenyloxy group, a 2-propenyloxy group, a 1-propenyloxy group, and a 1-methylvinyloxy group are preferable, and an ethenyloxy group and a 1-propenyloxy group are more preferable.

The term "$C_{2-6}$ alkynyloxy group" refers to a group with an oxygen atom to which a $C_{2-6}$ alkynyl group is bonded. Specific examples thereof include an ethynyloxy group, a 1-propynyloxy group, a 2-propynyloxy group, a butynyloxy group, a 1,3-pentanediynyloxy group, a 1,4-hexadiynyloxy group, a pentynyloxy group, and a hexynyloxy group. Among them, an ethynyloxy group, a 1-propynyloxy group, a 2-propynyloxy group, and a butynyloxy group are preferable, and an ethynyloxy group and a 2-propynyloxy group are more preferable.

The term "$C_{1-6}$ alkylthio group" refers to a group with a sulfur atom to which a $C_{1-6}$ alkyl group is bonded. Specific examples thereof include a methylthio group, an ethylthio group, a propylthio group, an isopropylthio group, a butylthio group, a sec-butylthio group, a tert-butylthio group, a pentylthio group, an isopentylthio group, and a hexylthio group. Among them, a methylthio group, an ethylthio group, a propylthio group, and a tert-butylthio group are preferable, and a methylthio group and an ethylthio group are more preferable.

The term "$C_{3-8}$ cycloalkylthio group" refers to a group with a sulfur atom to which a $C_{3-8}$ cycloalkyl group is bonded. Specific examples thereof include a cyclopropylthio group, a cyclobutylthio group, a cyclopentylthio group, a cyclohexylthio group, and a cyclooctylthio group. Among them, a cyclopropylthio group, a cyclobutylthio group, a cyclopentylthio group, and a cyclohexylthio group are preferable, and a cyclopropylthio group and a cyclobutylthio group are more preferable.

The term "$C_{2-6}$ alkenylthio group" refers to a group with a sulfur atom to which a $C_{2-6}$ alkenyl group is bonded. Specific examples thereof include an ethenylthio group, a 2-propenylthio group, a 1-propenylthio group, a 1-methylvinylthio group, a 1-butenylthio group, a 2-butenylthio group, a 3-butenylthio group, a 1,3-pentadienylthio group, a 1,4-hexadienylthio group, a 5-pentenylthio group, and a 6-hexenylthio group. Among them, an ethenylthio group, a 2-propenylthio group, a 1-propenylthio group, and a 1-methyl vinylthio group are preferable, and an ethenylthio group and a 1-propenylthio group are more preferable.

The term "$C_{2-6}$ alkynylthio group" refers to a group with a sulfur atom to which a $C_{2-6}$ alkynyl group is bonded. Specific examples thereof include an ethynylthio group, a 1-propynylthio group, a 2-propynylthio group, a butynylthio group, a 1,3-pentanediynylthio group, a 1,4-hexadiynylthio group, a pentynylthio group, and a hexynylthio group. Among them, an ethynylthio group, a 1-propynylthio group, a 2-propynylthio group, and a butynylthio group are preferable, and an ethynylthio group and a 2-propynylthio group are more preferable.

The term "$C_{1-6}$ alkylcarbonyloxy group" refers to a carbonyloxy group to which a $C_{1-6}$ alkyl group is bonded. Specific examples thereof include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, an isopentylcarbonyloxy group, and a hexylcarbonyloxy group. Among them, a methylcarbonyloxy group, an ethylcarbonyloxy group, a propylcarbonyloxy group, and a tert-butylcarbonyloxy group are preferable, and a methylcarbonyloxy group and an ethylcarbonyloxy group are more preferable.

The term "$C_{1-6}$ alkylcarbonyl group" refers to a carbonyl group to which a $C_{1-6}$ alkyl group is bonded. Specific examples thereof include a methylcarbonyl group, an ethylcarbonyl group, a propylcarbonyl group, an isopropylcarbonyl group, a butylcarbonyl group, a sec-butylcarbonyl group, a tert-butylcarbonyl group, a pentylcarbonyl group, an isopentylcarbonyl group, and a hexylcarbonyl group. Among them, a methyl-carbonyl group, an ethylcarbonyl group, a propylcarbonyl group, and a tert-butylcarbonyl group are preferable, and a methylcarbonyl group and an ethylcarbonyl group are more preferable.

The term "$C_{1-6}$ alkylamino group" refers to a group with a nitrogen atom to which a $C_{1-6}$ alkyl group is bonded. Specific examples thereof include an N-methylamino group, an N-ethylamino group, an N-propylamino group, an N-isopropylamino group, an N-butylamino group, an N-sec-butylamino group, an N-tert-butylamino group, an N-pentylamino group, an N-isopentylamino group, and an N-hexylamino group. Among them, an N-methylamino group, an N-ethylamino group, an N-propylamino group, and an N-tert-butylamino group are preferable, and an N-methylamino group and an N-ethylamino group are more preferable.

The term "di-$C_{1-6}$ alkylamino group" refers to a group with a nitrogen atom to which two $C_{1-6}$ alkyl groups are bonded. The two alkyl groups bonded to an amino group may be identical or different. Specific examples thereof include an N,N-dimethylamino group, an N-ethyl-N-methylamino group, an N,N-diethylamino group, an N,N-dipropylamino group, an N,N-diisopropylamino group, an N,N-dibutylamino group, an N,N-di-sec-butylamino group, an N,N-di-tert-butylamino group, an N,N-dipentylamino group, an N,N-diisopentylamino group, and an N,N-dihexylamino group. Among them, an N,N-dimethylamino group, N-ethyl-N-methylamino group, an N,N-diethylamino group, an N,N-dipropylamino group, and an N,N-di-tert-butylamino group are preferable, and an N,N-dimethylamino group, an N,N-diethylamino group, and an N-ethyl-N-methylamino group are more preferable.

The term "$C_{1-6}$ alkylsulfinyl group" refers to a sulfinyl group (—SO—) to which a $C_{1-6}$ alkyl group is bonded. Specific examples thereof include a methanesulfinyl group, an ethanesulfinyl group, a propanesulfinyl group, an isopropanesulfinyl group, a butane-sulfinyl group, a sec-butanesulfinyl group, a tert-butanesulfinyl group, a pentane-sulfinyl group, an isopentanesulfinyl group, and a hexanesulfinyl group. Among them, a methanesulfinyl group, an ethanesulfinyl group, a propanesulfinyl group, and a tert-butanesulfinyl group are preferable, and a methanesulfinyl group and an ethanesulfinyl group are more preferable.

The term "$C_{1-6}$ alkylsulfonyl group" refers to a sulfonyl group (—$SO_2$—) to which a $C_{1-6}$ alkyl group is bonded. Specific examples thereof include a methanesulfonyl group, an ethanesulfonyl group, a propanesulfonyl group, an isopropanesulfonyl group, a butane-sulfonyl group, a sec-butanesulfonyl group, a tert-butanesulfonyl group, a pentane-sulfonyl group, an isopentanesulfonyl group, and a hexanesulfonyl group. Among them, a methanesulfonyl group, an ethanesulfonyl group, a propanesulfonyl group, and a tert-butanesulfonyl group are preferable, and a methanesulfonyl group and an ethane-sulfonyl group are more preferable.

The term "$C_{3-8}$ cycloalkylsulfinyl group" refers to a sulfinyl group to which a $C_{3-8}$ cycloalkyl group is bonded. Specific examples thereof include a cyclopropanesulfinyl group, a cyclobutanesulfinyl group, a cyclopentanesulfinyl group, a cyclohexane-sulfinyl group, and a cyclooctanesulfinyl group. Among them, a cyclopropanesulfinyl group, a cyclobutanesulfinyl group, a cyclopentanesulfinyl group, and a cyclohexane-sulfinyl group are preferable, and a cyclopropanesulfinyl group and a cyclobutane-sulfinyl group are more preferable.

The term "$C_{3-8}$ cycloalkylsulfonyl group" refers to a sulfonyl group to which a $C_{3-8}$ cycloalkyl group is bonded. Specific examples thereof include a cyclopropanesulfonyl group, a cyclobutanesulfonyl group, a cyclopentanesulfonyl group, a cyclohexane-sulfonyl group, and a cyclooctane-sulfonyl group. Among them, a cyclopropanesulfonyl group, a cyclobutanesulfonyl group, a cyclopentanesulfonyl group, and a cyclohexane-sulfonyl group are preferable, and a cyclopropanesulfonyl group and a cyclobutane-sulfinyl group are more preferable.

The term "$C_{1-6}$ alkyloxycarbonyl group" refers to a carboxyl group to which a $C_{1-6}$ alkyl group is bonded via an ester bond. Specific examples thereof include a methyloxycarbonyl group, an ethyloxycarbonyl group, a propyloxycarbonyl group, an iso-propyloxycarbonyl group, a butyloxycarbonyl group, a sec-butyloxycarbonyl group, a tert-butyloxycarbonyl group, a pentyloxycarbonyl group, an isopentyloxycarbonyl group, and a hexyloxycarbonyl group. Among them, a methyloxycarbonyl group, an ethyloxycarbonyl group, a propyloxycarbonyl group, and a tert-butyloxycarbonyl group are preferable, and a methyloxycarbonyl group and an ethyloxycarbonyl group are more preferable.

The term "$C_{6-14}$ aryl group" refers to an aromatic hydrocarbon group containing 6 to 14 carbons. Specific examples thereof include a phenyl group, a naphthyl group, and an anthranyl group. Among them, a phenyl group and a naphthyl group are preferable, and a phenyl group is more preferable.

The term "$C_{7-20}$ aralkyl group" refers to a $C_{1-6}$, preferably $C_{1-4}$ alkyl group to which a $C_{6-14}$, preferably $C_{6-10}$ aryl group is bonded. It is preferably a $C_{7-14}$ aralkyl group. Specific examples thereof include a benzyl group, a phenethyl group, or a naphthylmethyl group.

In the present specification, even when a group is described only as a $C_{1-6}$ alkyl as in "$C_{1-6}$ alkylcarbonyloxy group" and the like, the $C_{1-6}$ alkyl can also be substituted with a cycloalkyl of a $C_{3-8}$ ring moiety, or a $C_{3-8}$ cycloalkyl such as a $C_{3-8}$ cycloalkyl $C_{1-2}$ alkyl.

In the formula (I), $R_1$ and $R_2$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, (31) a $C_{7-20}$ aralkyl group or (32) a carboxyl ion. Among them, (1) a hydrogen atom, (3) a hydroxyl group, (5) a nitro group, (6) an amino group, (7) a $C_{1-6}$ alkyl group, (11) a $C_{1-6}$ alkoxy group, (12) a $C_{3-8}$ cycloalkoxy group, (22) a $C_{1-6}$ alkylamino group, (23) a di-$C_{1-6}$ alkylamino group, or (29) a $C_{1-6}$ alkyloxycarbonyl group is preferable, and (1) a hydrogen atom, (5) a nitro group, (6) an amino group, (7) a $C_{1-6}$ alkyl group, (22) a $C_{1-6}$ alkylamino group, or (23) a di-$C_{1-6}$ alkylamino group, or (29) a $C_{1-6}$ alkyloxycarbonyl group is more preferable.

In the formula (I), $R_3$ and $R_4$ are the same as or different from each other and each independently represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, (7) a $C_{7-20}$ aralkyl group or (8) a negative charge. Among them, (1) a hydrogen atom, (2) a $C_{1-6}$ alkyl group or (7) a $C_{7-20}$ aralkyl group or (8) a negative charge is preferable, and (1) a hydrogen atom or (8) a negative charge is more preferable.

In the formula (I), $X_1$ and $X_2$ are the same as or different from each other and each independently represents the following structure.

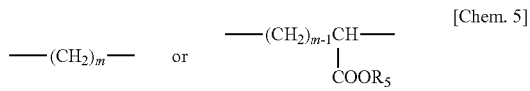

[Chem. 5]

In the above structure, m represents an integer of 1 to 6, preferably an integer of 1 or 2.

In the above structure, $R_5$ represents (1) a hydrogen atom, (2) a $C_{1-6}$ alkyl group, (3) a $C_{3-8}$ cycloalkyl group, (4) a $C_{2-6}$ alkenyl group, (5) a $C_{2-6}$ alkynyl group, (6) a $C_{6-14}$ aryl group, (7) a $C_{7-20}$ aralkyl group or (8) a negative charge. Among them, (1) a hydrogen atom or (8) a negative charge is preferable.

In the formula (I), M represents a divalent or trivalent rare earth metal ion.

A rare earth metal collectively refers to 17 elements consisting of a group of 15 elements from lanthanum having an atomic number of 57 to lutetium having an atomic number of 71 (lanthanides), and two additional elements consisting of scandium having an atomic number of 21 and yttrium having an atomic number of 39. Specific examples of rare earth metals include europium, terbium, lanthanum, cerium, praseodymium, neodymium, promethium, samarium, gadolinium, dysprosium, holmium, erbium, thulium, ytterbium, lutetium, scandium and yttrium, with europium and terbium being preferable, and europium being more preferable.

The rare earth metal ion is used as a divalent or trivalent, and preferably a trivalent, rare earth metal ion, and coordinates with a phenanthroline compound.

The rare earth metal is present as the central metal of the rare earth metal complex, and is coordinated to a heteroatom on an intramolecular ring in the phenanthroline compound functioning as a ligand.

Although the rare earth metal is represented by the letter M shown inside the broken line circle in the rare earth metal complex represented by the formula (I), this description means that the rare earth metal is coordinate-bonded to a nitrogen atom within the phenanthroline structure. In addition, the rare earth metal may also be present in the form of a cation in the rare earth metal complex, and may be coordinate bonded to a ligand containing an atom such as a nitrogen atom, oxygen atom or sulfur atom. An example of such a rare earth metal complex may be a complex having the structure shown below.

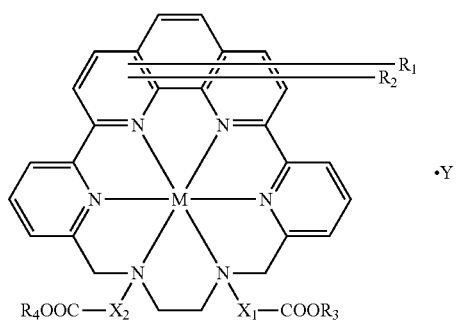

[Chem. 6]

In the above structure, although the rare earth metal is depicted so as to be coordinated with all of the nitrogen atoms within the phenanthroline structure, this is merely disclosed as one aspect of the rare earth metal complex of the present invention, and the present invention is not limited to this structure.

In addition, in the rare earth metal complex of the present invention, the rare earth metal may also be coordinate-bonded to a ligand containing an atom such as a nitrogen atom, oxygen atom or sulfur atom of $R_1$, $R_2$, $R_3$, $R_4$, $X_1$ or $X_2$ in addition to a nitrogen atom within the phenanthroline structure, or the rare earth metal may be coordinate-bonded to a ligand containing an atom such as a nitrogen atom, oxygen atom or sulfur atom of $R_1$, $R_2$, $R_3$, $R_4$, $X_1$ or $X_2$.

In formula (I), the rare earth metal complex of the present invention may also be a complex having the following structure when the case in which $R_3$ or $R_4$ represents a negative charge is described as one aspect of the present invention.

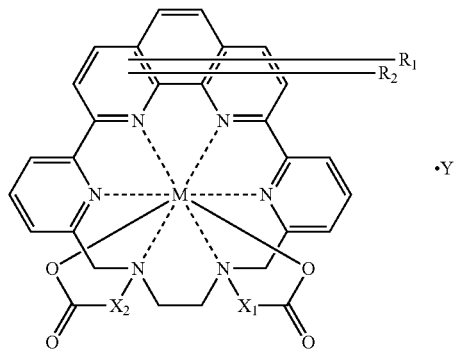

[Chem. 7]

The above-mentioned structure disclosed one aspect of the present invention, and although the rare earth metal complex of the present invention is not limited to only the above-mentioned structure, in the case $R_3$ and $R_4$ represent a negative charge, an oxygen atom having a negative charge may be coordinate-bonded to the rare earth metal.

In the above-mentioned structure, although coordinate bonds between the rare earth metal and nitrogen atoms within the phenanthroline structure are indicated with dotted lines in order to indicate the characteristic bonds between the moieties corresponding to $R_3$ and $R_4$ and the rare earth metal, this is not intended to mean that the dotted lines and the solid lines are substantially different structures.

In the formula (I), Y represents an anion or is not present, and examples of anions include halogen ions such as chlorine ions, iodine ions or bromine ions, nitrate ions, sulfate ions and acetate ions, with halogen ions being preferable. When an anion is present in the phenanthroline structure functioning as a ligand, Y forms a counter ion with a metal ion in the complex together with the anion.

The rare earth metal complex represented by formula (I) can be produced by carrying out a complex-forming reaction in accordance with ordinary methods.

In the rare earth metal complex represented by the formula (I), the ligand is the phenanthroline compound represented by the following formula (II). In one aspect of the present invention, a compound represented by formula (II) is provided together with the rare earth metal complex represented by formula (I).

The compound represented by formula (II) may be a salt thereof and refers to a base addition salt such as sodium salt, potassium salt or other alkaline metal salt or calcium salt, magnesium salt or other alkaline earth metal salt, or an acid addition salt such as a hydrochloride or sulfate, and examples thereof include salts of a hydroxyl group (and specifically, a phenolic hydroxyl group, for example) or a carboxyl group (—COOH) or basic group (and specifically, an NH group, for example) present in the compound represented by the following formula (II).

Formula (II)

[Chem. 8]

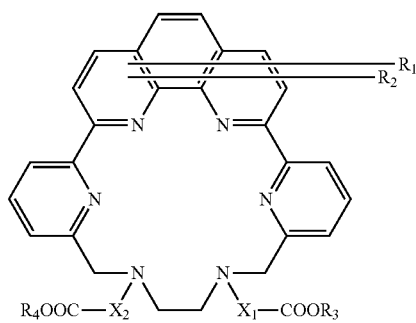

The rare earth metal complex represented by the formula (I) is a complex obtained by using, as preferable example of a ligand, 2,5-bis-carboxymethyl-2,5-diazo[6]-(5',5')-cyclo-2,9-di-(2'-pyridyl)-1,10-phenanthrolin ophane being a methylene group in which $R_1$, $R_2$, $R_3$ and $R_4$ are the same and represent hydrogen atoms, $X_1$ and $X_2$ are the same, and m is 1. In addition, compounds (26) and (28) disclosed in the following examples are examples of compounds preferably used as ligands.

The following provides an explanation of a production method of the rare earth metal complex represented by the above-mentioned formula (I).

The rare earth metal complex represented by the formula (I) can be obtained as a rare earth metal complex in which a rare earth metal is coordinated by mixing a compound represented by the above-mentioned formula (II) with a rare earth metal salt. The compound and the rare earth metal salt are preferably mixed at a ratio of 1:1 to 1:3. Examples of rare earth metal salts used in the reaction include chlorides, sulfates and acetates of rare earth metal elements, and chlorides are particularly preferable. The rare earth metal salt may be used by suitably mixing two or more types of metal salts. Examples of solvents used in the reaction include alcohol and water, and two or more types of solvents may be suitably used as a mixture thereof. Specific examples of alcohols include ethanol and methanol, and methanol is preferable. A mixed solvent of alcohol and water may also be used. Although there are no particular limitations on the reaction temperature, it is normally from room temperature to the boiling point of the solvent, and preferably from 20° C. to 60° C. Although there are no particular limitations on the reaction time, the reaction proceeds smoothly and is normally completed is about 10 minutes to 1 day.

A solution containing the rare earth metal complex emits light when irradiated with ultraviolet light. Concentration of this reaction solution results in precipitation of the desired rare earth metal complex. The rare earth metal complex of the present invention can then be obtained by separating from the reaction solution using ordinary separation means and drying the resulting solid.

As shown in the following scheme (I), the compound represented by the formula (II) that is used for producing a rare earth metal complex is producible by reacting a compound represented by the formula (III) with a compound represented by the formula (IV).

Further, the compound represented by the formula (II) is producible by, after reacting a compound represented by the formula (III) with a compound represented by the formula (IV), appropriately introducing and/or converting a desired substituent by an ordinary method.

Scheme (I):

[Chem.9]

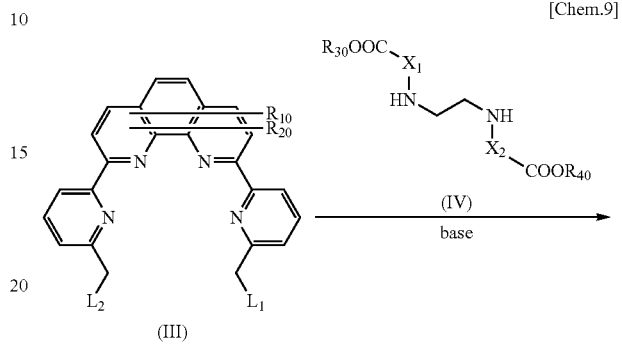

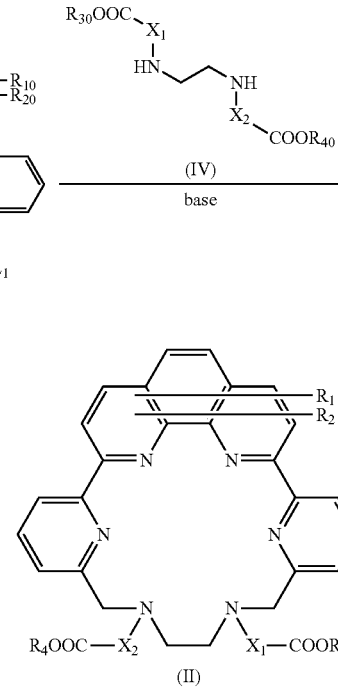

$R_1$ to $R_4$ as well as $X_1$ and $X_2$ in the scheme (I) represent the same groups as described above, and $R_{10}$ and $R_{20}$ are the same as or different from each other and each independently may be the same groups as $R_1$ and $R_2$, or groups that can be converted to groups represented by $R_1$ and $R_2$ such as those that are protected by protective groups.

$R_{30}$ and $R_{40}$ are the same as or different from each other and each independently may be the same groups as $R_3$ and $R_4$, or groups that can be converted to groups represented by $R_3$ and $R_4$ such as those that are protected by protective groups.

However, in the definitions of $R_1$ to $R_4$ (and in the same manner as previously described with respect to $R_{10}$, $R_{20}$, $R_{30}$ and $R_{40}$ as well) along with $X_1$ and $X_2$, since carboxyl ion and a negative charge are present during complex formation, they are excluded from the definitions in the production process of the ligand.

$L_1$ and $L_2$ are the same as or different from each other and each independently represents a leaving group.

Reactions in the scheme (I) can be carried out by reacting a compound represented by the formula (III) with a compound represented by the formula (IV) in an inert solvent in the presence of a base. The compound represented by the formula (IV) is preferably used in an amount of one to three equivalents, more preferable one to 1.5 equivalents relative to the compound represented by the formula (III).

The inert solvent used in the reaction is not particularly limited, as long as it allows the reaction of the compound represented by the formula (III) and the compound represented by the formula (IV) to smoothly proceed. Examples thereof include ethyl methyl ketone, acetonitrile, acetone, dimethylformamide, and dimethylacetamide. Among them, ethyl methyl ketone, acetonitrile, and acetone are preferable, and ethyl methyl ketone is more preferable.

Examples of base used in the reaction include alkaline metal carbonates such as sodium carbonate or potassium carbonate, alkaline earth metal carbonates such as calcium carbonate or magnesium carbonate, and organic alkylamines such as dimethylamine, diethylamine or triethylamine, sodium carbonate, potassium carbonate and magnesium carbonate are particularly preferable, and sodium carbonate is more preferable.

The base is preferably used in an amount of one to 10 equivalents, more preferable one to five equivalents relative to the compound represented by the formula (III).

Generally, the reaction is preferably carried out under non-aqueous conditions. The reaction is carried out preferably at from room temperature to the boiling point of the solvent, more preferably while heating under reflux. The reaction is completed in 10 hours to 10 days.

The compound represented by the formula (II) may be a compound directly produced by reacting the compound represented by the formula (IV) with the compound represented by the formula (III). As shown in the following scheme (II), after producing a compound represented by the formula (II-1), the compound can be converted to the desired compound represented by the formula (II) appropriately in accordance with an ordinary method.

Scheme (II):

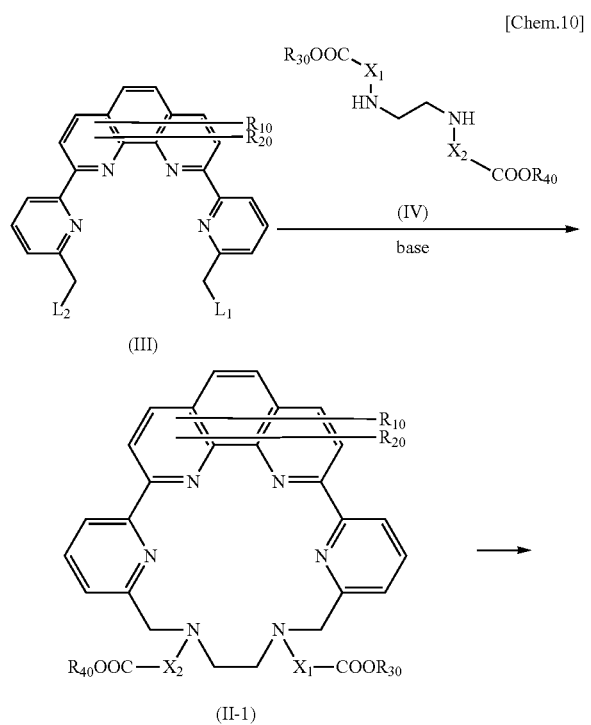

[Chem.10]

(III)

(IV)

(II-1)

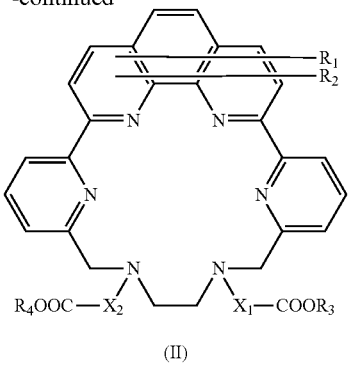

(II)

The compound represented by the formula (IV) may be a well-known or a commercially-available compound, or a compound that is producible in accordance with a known method or that can have desired $R_3$ and $R_4$ introduced thereinto or removed therefrom. $R_{30}$ and $R_{40}$ may be a protective group of a carboxyl group, and in the compound represented by the formula (II-1), $R_{30}$ and $R_{40}$ are deprotected to obtain a carboxyl group, and then $R_3$ and $R_4$ may be introduced.

In the production of the compound represented by the formula (II), $R_{30}$ and $R_{40}$ present in the compound represented by the formula (IV) used in the reaction may be a protective group of a carboxyl group. Examples thereof include a lower alkyl group such as a methyl group, an ethyl group, a propyl group, an isopropyl group, and a tert-butyl group; a halo-substituted lower alkyl group such as a 2,2,2-trichloroethyl group and a 2,2,2-trifluoroethyl group; a lower alkanoyloxyalkyl group such as an acetoxymethyl group, a propionyloxymethyl group, a pivaloyloxymethyl group, a 1-acetoxyethyl group, and a 1-propionyloxyethyl group; a lower alkoxycarbonyloxyalkyl group such as 1-(methoxycarbonyloxy)ethyl group, a 1-(ethoxycarbonyloxy)ethyl group, a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group, and a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group, and a bis(p-methoxyphenyl)methyl group; a (5-substituted-2-oxo-1,3-dioxol-4-yl)methyl group such as a (5-methyl-2-oxo-1,3-dioxol-4-yl)methyl group; a lower alkylsilyl group such as a trimethylsilyl group and a tert-butyldimethylsilyl group, an indanyl group, a phthalidyl group, and a methoxyethyl group.

Removal of the protective group of a carboxyl group differs depending on the kind of the protective group and the stability of the compound. In accordance with the method described in "Protective Groups In Organic Synthesis, Second Edition by T. W. Greene and P. G. M. Wuts, John Wiley&Sons, Inc." or a method according to the above method, removal of the protective group, but is not particularly limited to, can be carried out by, for example, a solvolysis reaction using an acid or a base, chemical reduction using a hydrogenated metal complex and the like, and catalytic reduction using a palladium carbon catalyst, a raney nickel catalyst, and the like. Examples of the base include an alkali metal hydroxide such as sodium hydroxide and potassium hydroxide.

The solvent to be used in the present process, but is not particularly limited to, is preferably an inert solvent that does not easily react with starting materials. Examples thereof include water, alcohols such as methanol, ethanol, isopropanol, and tert-butanol, ethers such as tetrahydrofuran, diethyl ether, diisopropyl ether, dioxane, and dimethoxyethane, halogenated hydrocarbons such as methylene chloride, chloroform, carbon tetrachloride, and 1,2-dichloroethane, hydrocarbons such as hexane, benzene, and toluene, ketones such as acetone and methyl ethyl ketone, nitriles such as acetonitrile, amides such as N,N-dimethylformamide, N,N-dimethylacetamide, N-methyl-2-pyrrolidone, and hexamethylphosphorylamide, and sulfoxides such as dimethyl sulfoxide, or a mixture of these solvents. Among them, alcohols such as methanol and ethers such as tetrahydrofuran and dimethoxyethane are preferable. The reaction temperature is preferably 0 to 100° C., more preferably 10 to 30° C. The reaction time is preferably 1 to 20 hours, more preferably 3 to 10 hours.

In the production of the compound represented by the formula (II), functional groups present in the compound represented by the formula (III) used in the reaction may be appropriately protected. As the protective group used in the reaction, one that is normally used as a protective group of, for example, a hydroxyl group, a carboxyl group, a carbonyl group, and an amino group can be employed. Examples thereof include, but are not particularly limited to, protective groups that are described in "Protective Groups In Organic Synthesis, Second Edition by T. W. Greene and P. G. M. Wuts, John Wiley&Sons, Inc."

Examples of the protective group of a hydroxyl group include, but are not particularly limited to, a methoxymethyl group, a methylthiomethyl group, a tetrahydrofuranyl group, a 1-ethoxyethyl group, a tert-butyldimethylsilyl group, a benzyl group, a tert-butyl group, an allyl group, and a triphenylmethyl group.

The protective group of a carboxyl group may be the protective group as described with respect to $R_{30}$ and $R_{40}$ above. Examples thereof include, but are not particularly limited to, a methyl group, an ethyl group, a 2,2,2-trichloroethyl group, an ethoxy-carbonyl group, a methoxycarbonyl group, a benzyl group, an o-nitrobenzyl group, a p-nitrobenzyl group, a b-p-toluenesulfonylethyl group, a p-methoxybenzyl group, and benzyloxycarbonyl.

Examples of the protective group of a carbonyl group include, but are not particularly limited to, a 1,3-dioxanyl group, a 5-methylene-1,3-dioxanyl group, and a 5,5-dibromo-1,3-dioxanyl group.

Examples of the protective group of an amino group include, but are not particularly limited to, an N-formyl group, an N-acetyl group, an N-chloroacetyl group, an N-benzoyl group, a tert-butyl group, an N-phthalimide group, a diphenylmethyl group, and a benzyl group. One or two of the above protective groups can be appropriately introduced to the amino group.

The leaving group is not particularly limited as long as it is a group that forms a C—N bond as it leaves, examples thereof include a halogen atom such as a fluorine atom, a chlorine atom, and a bromine atom, a trifluoroacetyl group, a methanesulfonyl group, a trifluoromethanesulfonyl group, a p-toluenesulfonyl group, and a diphenoxyphosphoryl group. Among them, a chlorine atom, a bromine atom, and a methane-sulfonyl group are preferable.

The compound represented by the formula (II) is producible in accordance with the following scheme (III).

Scheme (III):

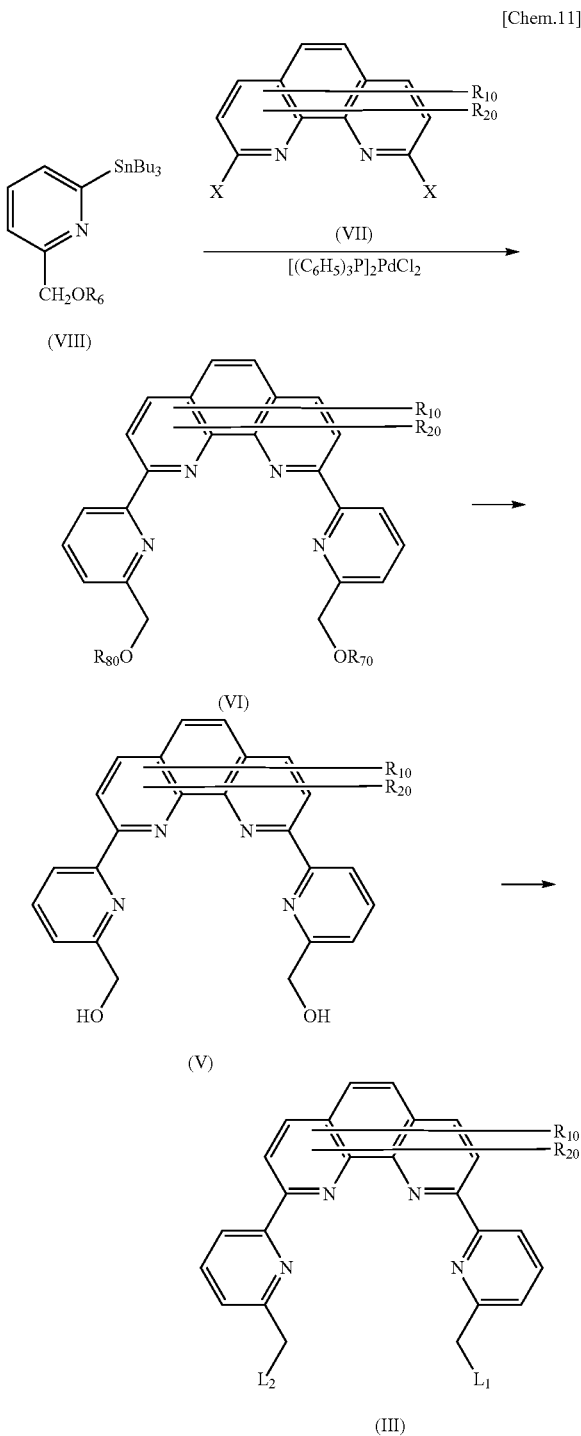

$R_{10}$ and $R_{20}$ as well as $L_1$ and $L_2$ in the scheme (III) represent the same groups as described above, and X represents a halogen atom.

Each of $R_6$, $R_{70}$, and $R_{80}$ independently represents a protective group of a hydroxyl group. $R_{70}$ and $R_{80}$ are the same as or different from each other and each independently represents a protective group of a hydroxyl group. Further, because $R_{70}$ and $R_{80}$ are derived from $R_6$ of the compound represented by the formula (VIII), both of $R_{70}$ and $R_{80}$ may be the same as $R_6$.

A compound having a phenanthroline structure represented by the following formula (II') or a salt thereof is useful as a key intermediate of a raw material compound for producing a rare earth metal complex.

Formula (II'):

[Chem.12]

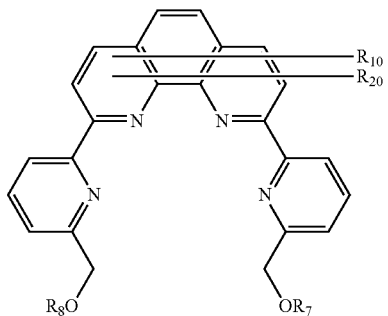

wherein, $R_{10}$ and $R_{20}$ are the same as or different from each other and each independently represents (1) a hydrogen atom, (2) a halogen atom, (3) a hydroxyl group, (4) a cyano group, (5) a nitro group, (6) an amino group, (7) a $C_{1-6}$ alkyl group, (8) a $C_{3-8}$ cycloalkyl group, (9) a $C_{2-6}$ alkenyl group, (10) a $C_{2-6}$ alkynyl group, (11) a $C_{1-6}$ alkoxy group, (12) a $C_{3-8}$ cycloalkoxy group, (13) a $C_{2-6}$ alkenyloxy group, (14) a $C_{2-6}$ alkynyloxy group, (15) a $C_{1-6}$ alkylthio group, (16) a $C_{3-8}$ cycloalkylthio group, (17) a $C_{2-6}$ alkenylthio group, (18) a $C_{2-6}$ alkynylthio group, (19) a $C_{1-6}$ alkylcarbonyloxy group, (20) a formyl group, (21) a $C_{1-6}$ alkylcarbonyl group, (22) a $C_{1-6}$ alkylamino group, (23) a di-$C_{1-6}$ alkylamino group, (24) a $C_{1-6}$ alkylsulfinyl group, (25) a $C_{1-6}$ alkylsulfonyl group, (26) a $C_{3-8}$ cycloalkylsulfinyl group, (27) a $C_{3-8}$ cycloalkylsulfonyl group, (28) a carboxyl group, (29) a $C_{1-6}$ alkyloxycarbonyl group, (30) a $C_{6-14}$ aryl group, or (31) a $C_{7-20}$ aralkyl group, or a group that can be converted to the group (1) to (31).

$R_7$ and $R_8$ are the same as or different from each other and each independently represents a hydrogen atom or a protective group.

$R_7$ and $R_8$ may be groups derived from $R_{70}$ and $R_{80}$ of the compound represented by the formula (VI), and the compound represented by the formula (II') encompasses the compound represented by the formula (VI) and the compound represented by the formula (V).

The compound represented by the formula (III) is producible by subjecting the compound represented by the formula (VIII) and the compound represented by the formula (VII) to a coupling reaction in the presence of triphenylphosphine palladium dichloride to produce the compound represented by the formula (VI), and removing a protective group of a hydroxyl group of the compound represented by the formula (VI), and subsequently converting the hydroxyl group to a leaving group.

Reactions of the compound represented by the formula (VIII) and the compound represented by the formula (VII) can be carried out in an inert solvent in the presence of triphenylphosphine palladium dichloride.

The compound represented by the formula (VIII) is preferably used in an amount of one to five equivalents, more preferable one to three equivalents relative to the compound represented by the formula (VII).

The solvent used in the reaction is not particularly limited as long as it allows the reaction of the compound represented by the formula (VIII) and the compound represented by the formula (VII) to smoothly proceed, but examples thereof include dimethylformamide, benzene, toluene, and ethylene chloride. Among them, dimethyl-formamide is preferable.

Generally, the reaction is preferably carried out in non-aqueous conditions. The reaction is carried out preferably at from room temperature to the boiling point of the solvent, more preferably while heating under reflux. The reaction is completed in 1 hour to 3 to 5 days.

Reactions to remove the protective group of a hydroxyl group of the compound represented by the formula (VI) can be carried out in an inert solvent in the presence of an acid.

Examples of the inert solvent used in the reaction include, but is not particularly limited to, alcohols such as methanol, ethyl methyl ketone, acetonitrile, acetone, dimethylformamide, and dimethylacetamide. Among them, methanol is preferable.

The acid is preferably used in an amount of one to five equivalents, more preferable one to three equivalents relative to the compound represented by the formula (VI).

Generally, the reaction is carried out preferably at from room temperature to the boiling point of the solvent, more preferably while heating. The reaction is completed in 1 to 24 hours.

The compound represented by the formula (VII) is producible by producing phenanthroline by the methods described in literatures such as:

(1) Dictionary of Organic Compounds, 6$^{th}$ edition, Vol. 5, published by Chapman and Hall, London, UK, 1996, pages 5167-5168; and (2) Dai yuki kagaku, Vol. 16, Fukusokanshiki kagobutu (Heterocyclic Compound) III, Asakura Publishing Co., Ltd., April 1964, supervised by Munio KOTAKE, pages 356-363 (Terms in the parentheses are literal translation), and then halogenating the 2- and 9-positions of a phenanthroline ring by the methods described in literatures such as J. C. S. Perkin I, pages 976-978, 1974.

The compound represented by the formula (VIII) is producible by a conventionally known method in accordance with the following scheme (IV), using (6-halopyridine-2-yl) methanol as a starting material.

Scheme (IV):

[Chem.13]

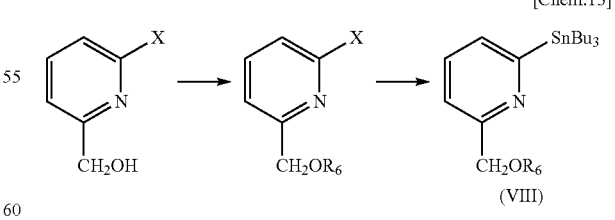

wherein X represents a halogen atom and $R_6$ represents a protective group of a hydroxyl group.

A method for converting a hydroxyl group of the compound represented by the formula (V) to a leaving group can be carried out by an ordinary method. For example, the method can be carried out by reacting a halide such as thionyl halide such as thionyl chloride and thionyl bromide and a sulfonic acid halide such as p-toluenesulfonyl chloride and p-toluenesulfonyl bromide with the compound represented by the formula (V) in the presence of a base. The halide to be employed in the reaction is preferably used in an amount of one to five equivalents, more preferable one to three equivalents relative to the compound represented by the formula (V).

The solvent used in the reaction is not particularly limited as long as it allows the reaction of the compound represented by the formula (V) and the halide to smoothly proceed, but examples thereof include methylene chloride, chloroform, ethyl methyl ketone, acetonitrile, acetone, dimethylformamide, and dimethylacetamide. Among them, methylene chloride, ethyl methyl ketone, acetonitrile, and acetone are preferable, among which methylene chloride is more preferable.

Examples of the base to be used in the reaction include an alkali metal carbonate salt such as sodium carbonate and potassium carbonate, an alkaline earth metal carbonate salt such as calcium carbonate and magnesium carbonate, and organic alkylamine such as dimethylamine, diethylamine, and triethylamine. Among them, sodium carbonate, potassium carbonate, magnesium carbonate, triethylamine, and the like are preferable, among which triethylamine is more preferable.

The base is preferably used in an amount of one to 10 equivalents, more preferable one to five equivalents relative to the halide. Generally, the reaction is preferably carried out in nonaqueous conditions. The reaction is carried out preferably at from room temperature to the boiling point of the solvent, more preferably while heating under reflux. The reaction is completed in 10 hours to 5 days.

The compound represented by the formula (IV) is producible by a conventionally known method in accordance with the following scheme (V).

Scheme (V):

[Chem.14]

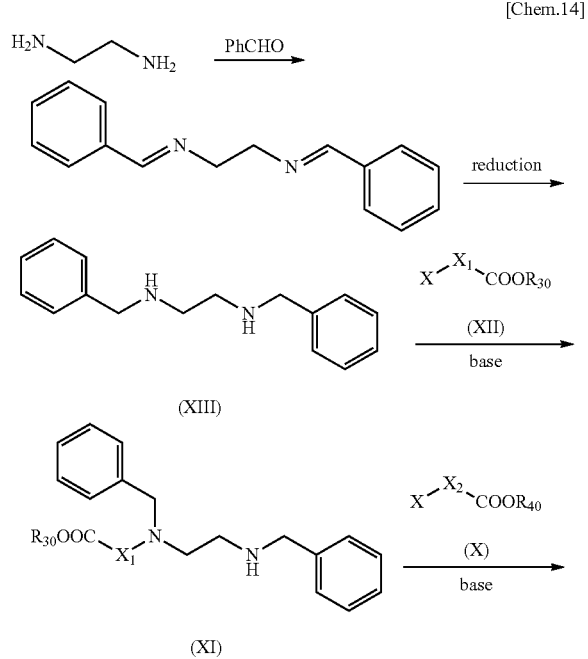

(XI)

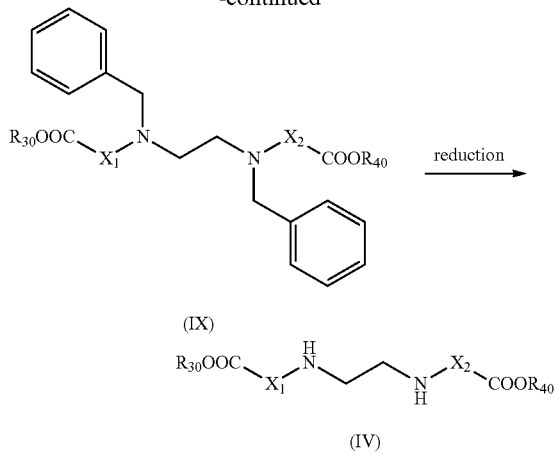

wherein $R_{30}$, $R_{40}$, $X_1$ and $X_2$ represent the same groups as described above, and X represents a halogen atom.

The compound represented by the formula (IV) is producible by alkylating the compound represented by the formula (XIII) obtainable from ethylenediamine sequentially with the compound represented by the formula (XII) and the compound represented by the formula (X) to produce the compound represented by the formula (IX), and then removing an N-benzyl protective group of an amino group of the compound represented by the formula (IX).

Reactions of the compound represented by the formula (XIII) and the compound represented by the formula (XII) can be carried out in an inert solvent in the presence of a base.

The compound represented by the formula (XII) is used in an amount of one to five equivalents, preferably one to three equivalents relative to the compound represented by the formula (XIII)

The solvent used in the reaction is not particularly limited as long as it allows the reaction of the compound represented by the formula (XIII) and the compound represented by the formula (XII) to smoothly proceed, but examples thereof include acetonitrile, dimethylformamide, benzene, toluene, and methylene chloride. Among them, acetonitrile is preferable. Generally, the reaction is preferably carried out in nonaqueous conditions. The reaction is carried out preferably at from room temperature to the boiling point of the solvent, more preferably while heating under reflux. The reaction is completed in 1 hour to 3 to 5 days.

Reactions of the compound represented by the formula (XI), which is obtainable by reactions of the compound represented by the formula (XIII) and the compound represented by the formula (XII), and the compound represented by the formula (X) can be carried out in a similar manner to the reactions of the compound represented by the formula (XIII) and the compound represented by the formula (XII).

Reactions for removing an N-benzyl protective group of an amino group of the compound represented by the formula (IX) can be carried out by a conventionally known hydrogen-reduction reaction.

Abbreviations used in the present invention have the meanings of the abbreviations commonly used in the art.

EXAMPLES

Hereinafter, the present invention will be described in detail with Examples. However, the present invention will not be limited to these Examples.

Metal Insertion Procedure

Example 1

A 500 mmol/L aqueous solution of europium chloride was added to 10 mL of an aqueous solution of compound (24) (18.7 mg, 35 mmol) so as to obtain europium chloride ($EuCl_3$, 25.6 mg, 70 mmol). The reaction solution was stirred for 1 hour at 50° C. and then stirred overnight at room temperature to synthesize a europium complex.

Residue obtained by concentrating under reduced pressure was eluted with methanol using LH-20 to obtain a europium complex having the prescribed compound (24) as a ligand thereof that was designated as complex 1.

ESIMS (positive) m/z: 684.8, (M+H) (F.W=684.5 for $C_3OH_{24}EuN_6O_4$) (Waters, LCT Premier, column: Tosoh ODS-100V)

Compounds (26) and (28) were also obtained as europium complexes using the same method as that for compound (24) and were designated as complex 2 and complex 3, respectively.

Fluorescence Property of Complex

Example 2

The result of measuring the fluorescence spectrum of an aqueous methanol solution (1 mmol/L, methanol content: 6%) of complex 1 at an excitation wavelength of 360 nm with a fluorescence spectrophotometer (Model F-7000, Hitachi High-Technologies Corp.) is shown in FIG. 1.

As shown in FIG. 1, an intense emission of red light was observed from europium ion in the vicinity of 620 nm.

Figure 2:
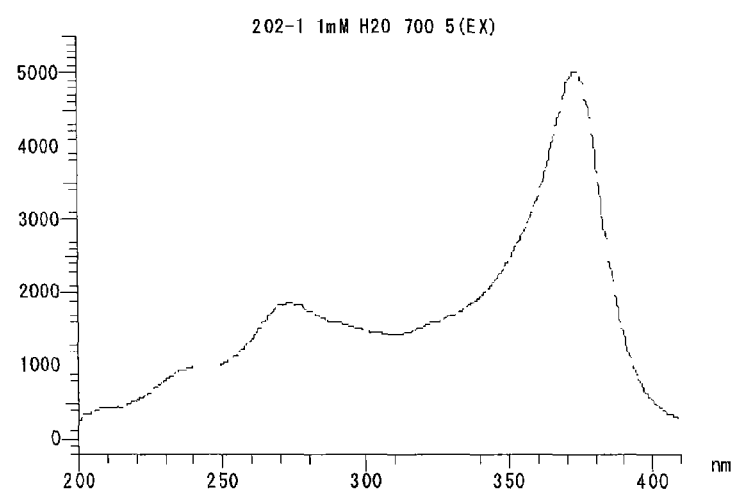
FIG. 2 shows the result of measuring the excitation spectrum at a fluorescence wavelength of 620 nm when complex 1 was fluoresced at an excitation wavelength of 360 nm.

In addition, the result of measuring the excitation spectrum at 620 nm in the vicinity of the peak wavelength of the fluorescence spectrum is shown in FIG. 2.

As shown in FIG. 2, the excitation spectrum was confirmed to 400 nm or more, demonstrating a peak in the vicinity of 380 nm, and the excitation spectrum was confirmed to include the visible region.

Figure 3:
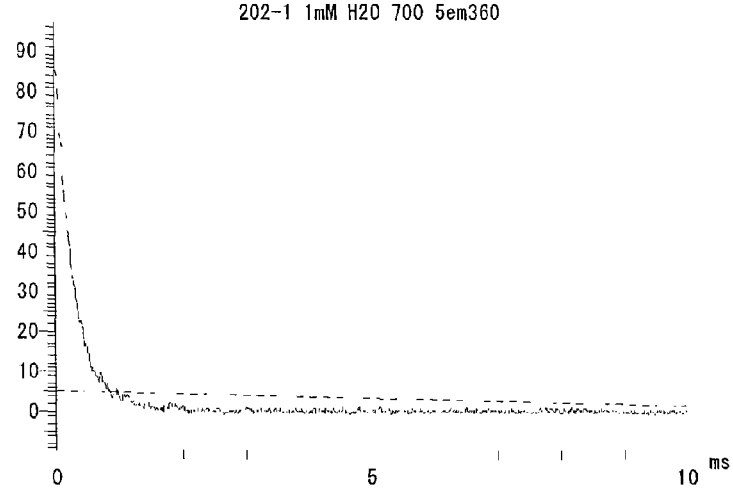
FIG. 3 shows the result of measuring the fluorescence life of complex 1 at an excitation wavelength of 360 nm.

The result of measuring the fluorescence life at an excitation wavelength of 360 nm is shown in FIG. 3. The fluorescence life t at this time was 300 msec, thereby confirming that complex 1 has a long life in an aqueous solution.

Figure 4:
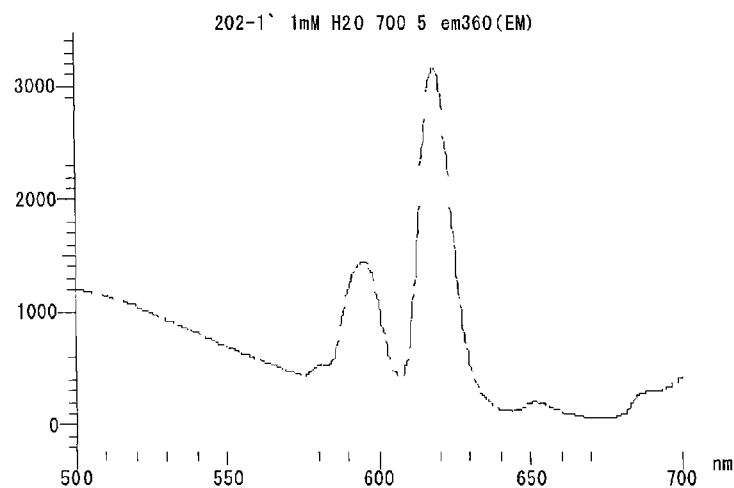
FIG. 4 shows the result of measuring the fluorescence spectrum of complex 2 at an excitation wavelength of 360 nm.
Figure 5:
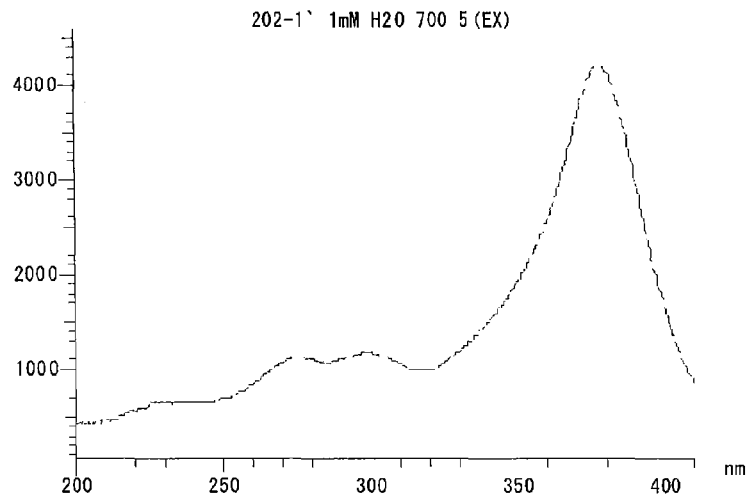
FIG. 5 shows the result of measuring the excitation spectrum at a fluorescence wavelength of 620 nm when complex 2 was fluoresced at an excitation wavelength of 360 nm.
Figure 6:
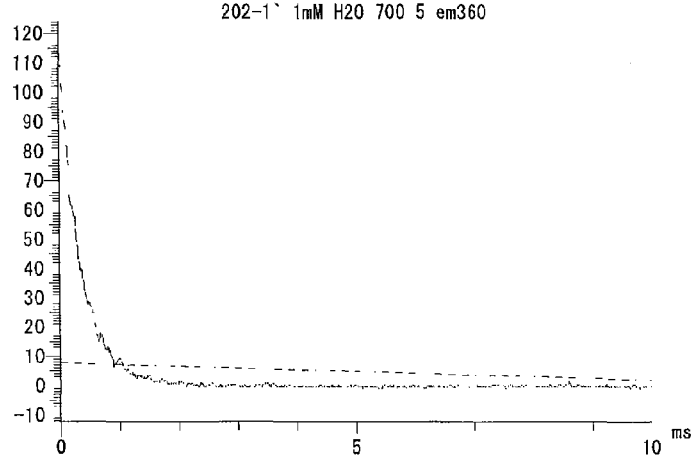
FIG. 6 shows the result of measuring fluorescence life of complex 2 at an excitation wavelength of 360 nm.

Similar measurements were carried out for an aqueous methanol solution (1 mmol/L, methanol content: 4%) of complex 2. Those results are shown in FIGS. 4, 5 and 6.

DNA Labeling and Others

Example 3

10 nmol of 5'-terminal amino-labeled oligo DNA (42-mer) and complex 1 (200 nmol) were allowed to react overnight in the presence of a condensation agent (DMT-MM, Wako Chemical, Ltd.) to label the oligo DNA with the complex 1 by binding thereto. Ethanol and 3 M aqueous sodium acetate solution (Nippon Gene Co., Ltd.) were added to the reaction solution followed by centrifugal separation to separate the labeled DNA by precipitation.

70% aqueous ethanol solution was then added to the resulting precipitate followed by centrifugal separation to again separate the labeled DNA by precipitation. The precipitate was then dissolved in water and purified by gel filtration (G-50). The ultraviolet absorption spectrum was measured for each of the purified fractions, the concentrations of oligo DNA were calculated from the values at 260 nm (ultraviolet absorption measurement: ND-1000, NanoDrop Technologies, Inc.).

Subsequently, aqueous solutions of the labeled oligo DNA were prepared and adjusted to concentrations of 100 nmol/L, 10 nmol/L and 1 nmol/L followed by measurement of count results at an excitation wavelength of 360 nm and fluorescence wavelength of 620 nm with a fluorescence spectrophotometer (Model F-7000, Hitachi High-Technologies Corp.).

Labeled oligo DNA was obtained for complex 2 and counts thereof were measured at a fluorescence wavelength of 620 nm in the same manner as complex 1. The results are shown in Table 1.

Comparative Example

Using a commercially available europium complex in the form of cryptate (CSI Bio Co., Ltd.), 63.7 nmol of (26.5 mM/L, 0.13 M Hepes solution (pH=8)) of cryptate TBP monosubetate (CSI Bio Co., Ltd.) were added to 4 nmol (1 mM/L, 0.25 M Hepes solution (pH=8)) of 5'-terminal amino-labeled oligo DNA (42-mer) and allowed to react overnight at room temperature in accordance with the manufacturer's recommended conditions. After diluting the reaction solution to 100 mL with 0.25 M Hepes solution (pH=8), the solution was purified by gel filtration (G-50) to label the oligo DNA. Subsequently, concentration was adjusted and fluorescence emission was measured using the same method as that of Example 3. The results are shown in Table 1.

TABLE 1

| Complex | 100 nmol/L | 10 nmol/L | 1 nmol/L |
|---------|------------|-----------|----------|
| Complex 1 | 742 | 77 | 12 |
| Complex 2 | 1158 | 120 | 14 |
| Cryptate | 208 | 21 | 8 |

Based on the measurement results, emission intensities of the oligo DNA labeled with complex 1 and complex 2 were confirmed to increase linearly from 1 nmol/L to 100 nmol/L.

Complex 1 and complex 2 were also able to be confirmed to have a superior fluorescence property with respect to a fluorescence property at an excitation wavelength of 360 nm even when compared with oligo DNA labeled with the commercially available europium complex.

The measurement in the following reference example and production examples are carried out under the following conditions unless specifically described.

Proton nuclear magnetic resonance spectra ($^1$H-NMR) were measured by INOVA500 Spectrometer (500 MHz) manufactured by Varian, Inc., and chemical shifts were recorded in units of d (ppm) relative to tetramethylsilane, and coupling constants were recorded in hertz (Hz).

Patterns have the following meanings; s; singlet, d; doublet, d.d; double doublet, t; triplet, m; multiplet, b; broad, and b.s; broad singlet.

High-performance liquid chromatography (HPLC) measurement was performed using LC-2010A HT manufactured by Shimadzu Corporation. The measurement conditions were as follows.

Column: YMC A302 S-5

UV: 254 nm

ESI-MS measurement was performed using LCMS-2010A manufactured by Shimadzu Corporation. As a column, Inertsil ODS-3 was employed.

Thin layer chromatography (TLC) was performed on a precoated silica gel plate (60E-254), and the results were visualized using UV light and ethanolic phosphomolybdic acid for detection.

Reference Example 1

(2,9-bis(6-((Methoxymethyloxy)methyl)pyridine-2-yl)-1,10-phenanthroline) (20)

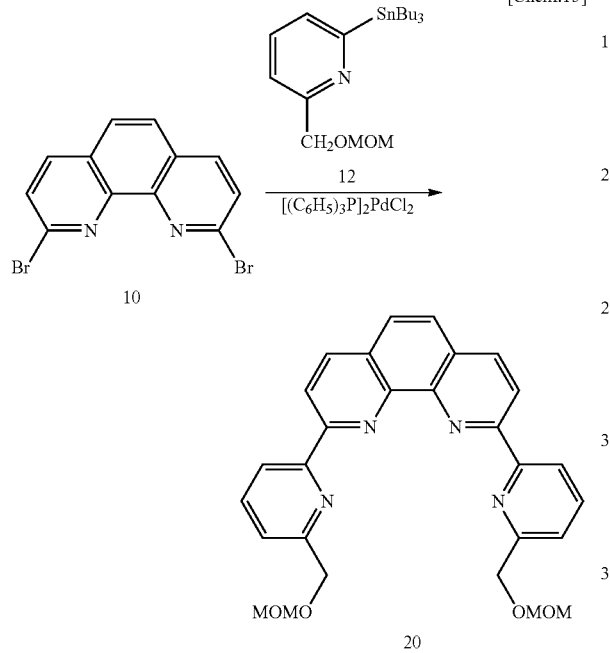

Under a stream of argon, 2,9-dibromo-1,10-phenanthroline (compound (10); 3.25 g; 9.6 mmol) was dissolved in anhydrous dimethylformamide (45 mL). To the reaction mixture, 2-methoxymethyloxymethylpyridine-6-yl tributyltin (compound (12); 17 g; 9.6 mmol) and triphenylphosphine palladium dichloride (3.83 g; 4.8 mmol) were added, followed by stirring at 70° C. for 22 hours. The reaction mixture was cooled to room temperature, and Rochelle salt was added thereto. Subsequently, the reaction mixture was poured into saline, and ethyl acetate was added thereto. Insoluble matters were filtered out, and the filtrate was extracted with ethyl acetate. The organic layer was washed with water and saturated saline, dried over anhydrous sodium sulfate, and then evaporated under reduced pressure to give oil matters. Under a stream of argon, the resulting oil matters were dissolved in anhydrous dimethylformamide (45 mL), and compound (12) (17 g; 9.6 mmol) and triphenylphosphine palladium dichloride (2.72 g; 3.38 mmol) were added thereto, followed by stirring at 70° C. for 20 hours. The reaction mixture was cooled to room temperature, and Rochelle salt was added thereto. Subsequently, the reaction mixture was poured into saline, and ethyl acetate was added thereto. Insoluble matters were filtered out, and the filtrate was extracted with ethyl acetate. The organic layer was washed with water and saturated saline, dried over anhydrous sodium sulfate, and then evaporated under reduced pressure to give a residue. The resulting residue was separated and purified by silica gel column chromatography ($SiO_2$, 200 g; developing solvent: chloroform/methanol=30/1 to 20/1 to 10/1), to give 1.1 g (yield: 23.7%) of the title compound (20).

$^1$H NMR (DMSO-$d_6$)d: 3.38 (s, 3H), 4.80-4.83 (m, 8H), 7.64 (d, J=8 Hz, 2H), 8.07-8.20 (m, 4H), 8.65-8.84 (m, 4H), 8.92 (d, J=7 Hz, 1H) HPLC mobile phase: 40-95% acetonitrile-water (0.1% trifluoroacetic acid)

Peak retention time: 5.7 minutes

ESIMS (positive) m/z 483.1, (M+H) (F.W=482.53 for $C_{28}H_{26}N_4O_4$)

2,9-bis(6-(Hydroxymethyl)pyridine-2-yl)-1,10-phenanthroline (21)

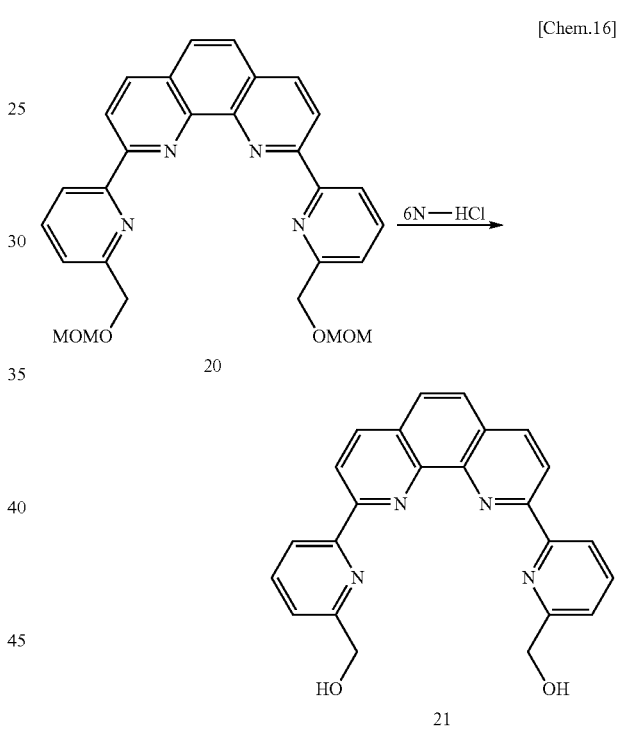

To compound (20) (1.09 g; 2.26 mmol), 6N-hydrochloric acid (5 mL) and methanol (25 mL) were added, and the resulting reaction mixture was stirred at 60° C. for 4 hours. The reaction mixture was evaporated under reduced pressure, and while there was some solvent left the mixture was made alkaline with a 5% aqueous sodium carbonate. Solids which precipitated out were separated by filtration. The resulting solids were dissolved in chloroform/methanol=3/1, insoluble matters were filtered out and the filtrate was evaporated under reduced pressure to give 0.72 g (yield: 81%) of the title compound (21).

$^1$H NMR (DMSO-$d_6$) d: 4.76 (d, J=5.5 Hz, 1H), 5.58 (t, J=6 Hz, 2H), 7.65 (d, J=7.5 Hz, 2H), 8.08 (s, 2H), 8.15 (t, J=7.5 Hz, 2H), 8.65 (d, J=8.5 Hz, 2H), 8.84 (d, J=8.5 Hz, 2H), 8.87 (d, J=8.5 Hz, 2H)

HPLC mobile phase: 30-80% acetonitrile-water (0.1% trifluoroacetic acid)

Peak retention time: 2.7 minutes

ESIMS (positive) m/z 395.1, (M+H) (F.W=394.43 for $C_{24}H_{18}N_4O_2$)

2,9-bis(6-(Chloromethyl)pyridine-2-yl)-1,10-phenanthroline (22)

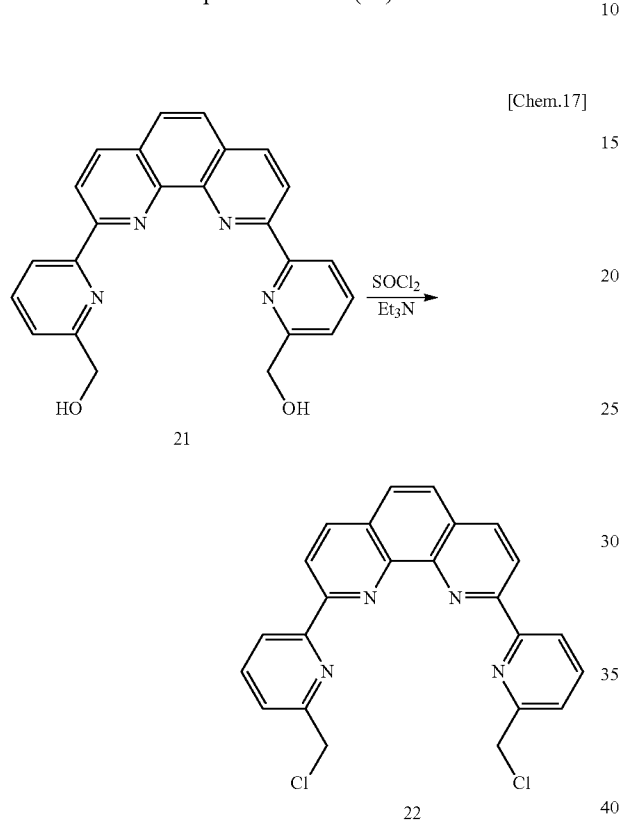

Under a stream of argon, compound (21) (0.7 g; 1.77 mmol) was suspended in methylene chloride (15 mL) in an ice bath. To the reaction mixture, triethylamine (0.54 g; 5.32 mmol) and thionyl chloride (0.51 g; 4.25 mmol) were sequentially added. The resulting reaction mixture was stirred at room temperature for 24 hours. The reaction mixture was made alkaline with a 5% aqueous sodium carbonate, and then evaporated under reduced pressure. The resulting residue was dissolved in chloroform/methanol=3/1, and inorganic matters were removed by membrane filtration. The filtrate was evaporated under reduced pressure to give a residue, and the resulting residue was separated and purified by silica gel column chromatography (SiO$_2$, 200 g) (chloroform/methanol=10/1 to 5/1 to 3/1) to give 0.49 g (yield: 64%) of the title compound (22).

$^1$H NMR (DMSO-d$_6$)d: 4.98 (s, 4H), 7.74 (d, J=7.5 Hz, 2H), 8.11 (s, 2H), 8.20 (t, J=7.5 Hz, 2H), 8.69 (t, J=8.5 Hz, 2H), 8.84 (t, J=8 Hz, 2H), 8.97 (d, J=8.5 Hz, 2H) HPLC mobile phase: 30-80% acetonitrile-water (0.1% trifluoroacetic acid) Peak retention time: 8.8 minutes ESIMS (positive) m/z: 432.09, (M+H) (F.W=431.32 for $C_{24}H_{18}Cl_2N_4$)

2,5-bis-tert-butyloxycarbonylmethyl-2,5-diazo[6]-(5',5')-cyclo-2,9-di-(2'-pyridyl)-1,10-phenanthrolinophane (23)

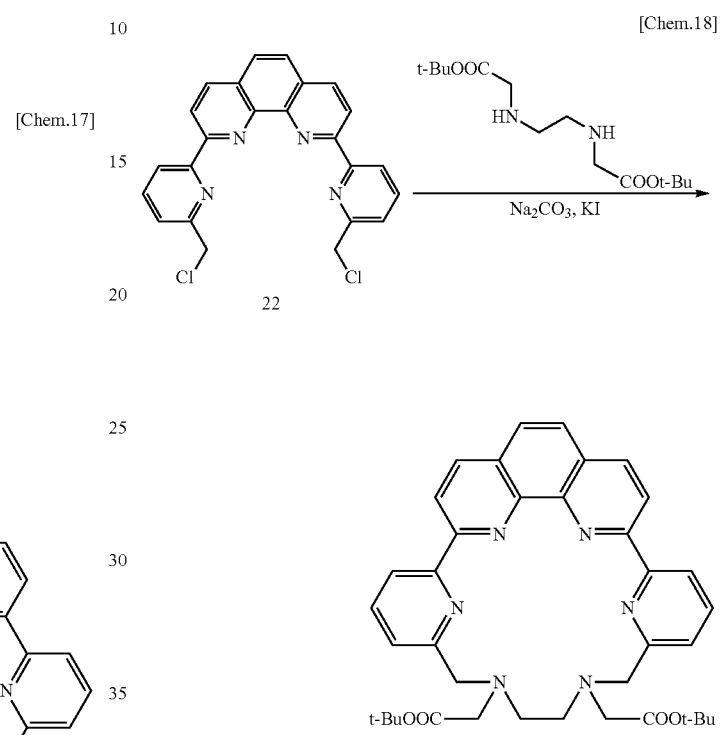

Under a stream of argon, compound (22) (0.71 g; 1.64 mmol) was dissolved in ethylmethylketone (100 mL). To the reaction mixture, N,N'-di-tert-butyloxycarbonylmethyl-1,2-ethylenediamine (0.81 g; 4.92 mmol), potassium iodide (0.82 g; 4.92 mmol), and sodium carbonate (0.87 g; 8.2 mmol) were added. The resulting reaction mixture was stirred and refluxed at 110° C. for 44 hours. The reaction mixture was cooled to room temperature and then insoluble matters were filtered out. The filtrate was evaporated under reduced pressure to give a residue, and the resulting residue was separated and purified by silica gel column chromatography (SiO$_2$, 200 g) (chloroform/methanol=20/1 to 10/1) to give 1.04 g (yield: 80%) of the title compound (23).

$^1$H NMR (CDCl$_3$)d: 1.53 (s, 18H), 2.91 (b.s, 4H), 3.52 (b.s, 4H), 4.10 (b.s, 4H), 7.34 (d, J=7.5 Hz, 2H), 7.57 (s, 2H), 7.61 (t, J=7.5 Hz, 2H), 8.17 (d, J=8.5 Hz, 2H), 8.74 (d, J=8.5 Hz, 2H), 8.80 (d, J=8.5 Hz, 2H)

HPLC mobile phase: 40-95% acetonitrile-water (0.1% trifluoroacetic acid)

Peak retention time: 12.2 minutes

ESIMS (positive) m/z 647.1, (M+H) (F.W=646.78 for $C_{38}H_{42}N_6O_4$)

2,5-bis-Carboxymethyl-2,5-diazo[6]-(5',5')-cyclo-2,9-di-(2'-pyridyl)-1,10-phenanthro linophane (24)

[Chem.19]

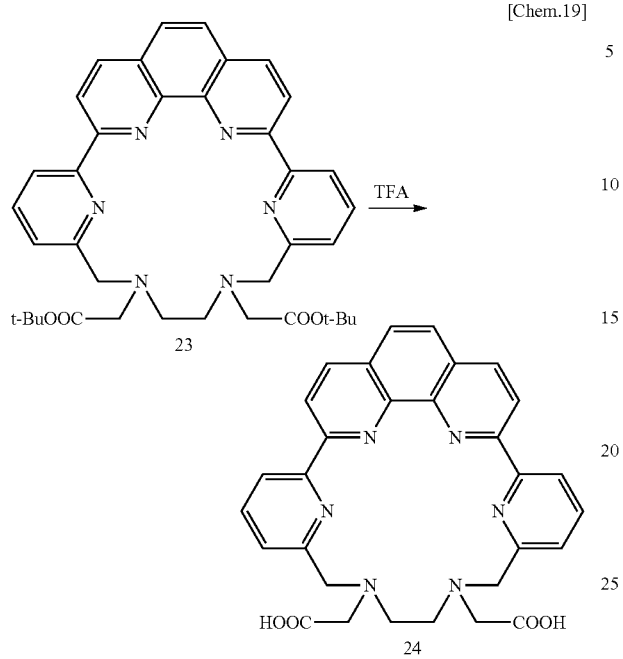

Under a stream of argon, 0.44 g of compound (23) was dissolved in methylene chloride (3.5 mL). To the reaction mixture, anisole (0.4 mL) and trifluoroacetic acid (1.5 mL) were added at room temperature. The resulting reaction mixture was stirred at room temperature for 19 hours. The reaction mixture was evaporated under reduced pressure and to the resulting residue was added 1N hydrochloric acid, and then the reaction mixture was evaporated under reduced pressure. Subsequently, using HP-20SS (30 mL), the resulting residue was eluted in an eluting solution of 10%, 20%=acetonitrile/water, and the fractions were collected and freeze-dried to give 150 mg of the title compound (24).

$^1$H NMR (DMSO-$d_6$)d: 3.04 (s, 4H), 3.61 (s, 4H), 4.08 (s, 4H), 7.23 (d, J=7.5 Hz, 2H), 7.47 (s, 2H), 7.66 (t, J=7.5 Hz, 2H), 8.09 (d, J=8.5 Hz, 2H), 8.35 (d, J=8.5 Hz, 2H), 8.46 (d, J=7.5 Hz, 2H)

HPLC mobile phase: 20-90% acetonitrile-water (0.1% trifluoroacetic acid)

Peak retention time: 5.3 minutes

ESIMS (positive) m/z: 535, (M+H) (F.W=534.57 for $C_{30}H_{26}N_6O_4$)

2,5-bis-tert-butyloxycarbonylmethyl-3-ethoxycarbonyl-2,5-diazo[6]-(5',5')-cyclo-2,9-di-(2'-pyridyl)-1,10-phenanthrolinophane (25)

[Chem.20]

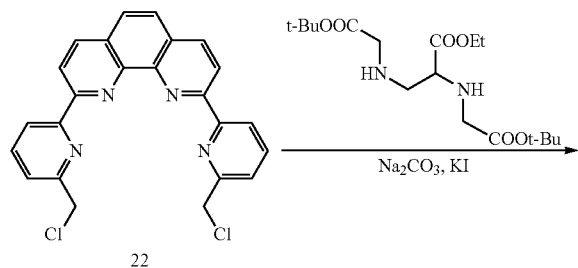

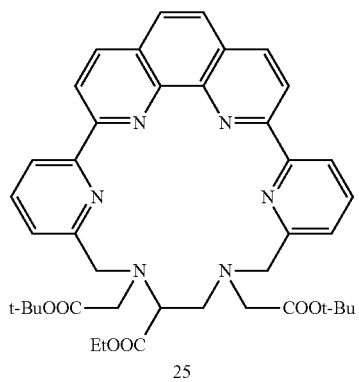

Under a stream of argon, compound (22) (30 mg, 70 mmol) was dissolved in ethyl methyl ketone (8 mL). To the reaction mixture, diethyleneamine derivative (75.2 mg, 209 mmol), potassium iodide (34.6 mg, 209 mmol) and sodium carbonate (36.9 mg, 348 mmol) were added. The resulting reaction mixture was stirred and refluxed for 21 hours at 85° C. The reaction mixture was cooled to room temperature, and the reaction mixture was extracted by addition of chloroform (5 mL) and water (5 mL). Moreover, the organic layer was further washed twice with water (5 mL). The organic layer was then concentrated under reduced pressure to obtain the crude title compound (25). This compound was then used in the next step without purifying.

HPLC mobile phase: 0-90% acetonitrile-water (0.1% trifluoroacetic acid)

Peak retention time: 20 minutes (Waters, Alliance 2695, column: Tosoh ODS-100V, 254 nm) ESIMS (positive) m/z: 719.4, (M+H) (F.W=718.8 for $C_{41}H_{46}N_6O_6$)

(Waters, LCT Premier, column: Tosoh ODS-100V)

2,5-bis-carboxymethyl-3-carboxy-2,5-diazo[6]-(5',5')-cyclo-2,9-di-(2'-pyridyl)-1,10-phenanthrolinophane (26)

[Chem. 21]

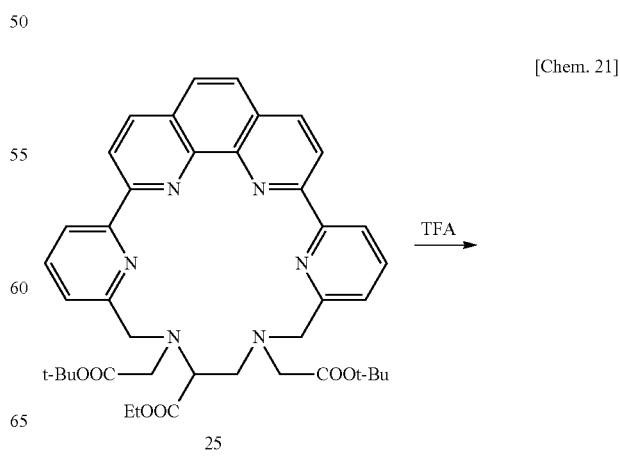

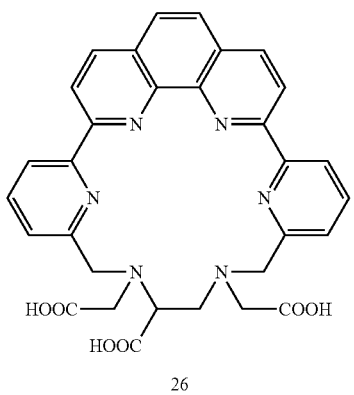

26

Under a stream of argon, compound (25) (50.3 mg) was suspended in dichloromethane (2.1 mL). To the reaction mixture, anisole (0.172 mL) and trifluoroacetic acid (0.046 mL) were added at room temperature. The resulting reaction mixture was stirred for 17 hours at the same temperature. The reaction mixture was then extracted by addition of chloroform (3 mL) and water (3 mL). Moreover, the organic layer was further extracted three times with 12 N hydrochloric acid (1 mL) and water (1 mL). The resulting aqueous phase was separated by column chromatography (LH-20/MeOH) to obtain an aqueous solution of the title compound (26).

[Chem. 22]

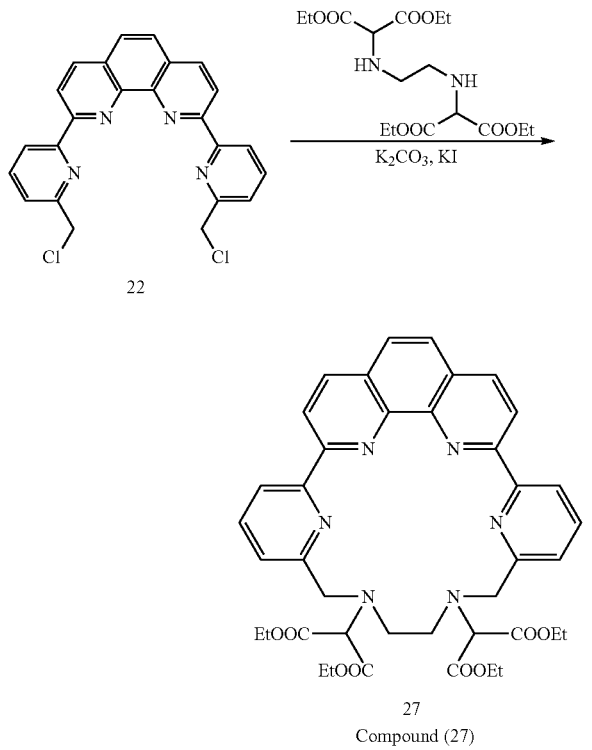

Compound (27)

Under a stream of argon, compound (22) (20 mg, 46 mmol) was dissolved in ethyl methyl ketone (7 mL). To the reaction mixture, diethyleneamine derivative (52.4 mg, 139 mmol), potassium iodide (23.1 mg, 139 mmol) and potassium carbonate (24.6 mg, 243 mmol) were added. The resulting reaction mixture was stirred and refluxed for 19 hours at 90° C. The reaction mixture was cooled to room temperature, and the reaction mixture was extracted by addition of chloroform (3 mL) and water (3 mL). Moreover, the organic layer was further washed twice with water (3 mL). The organic phase was concentrated under reduced pressure to obtain a crude compound (27). This compound was used in the next step without purifying.

HPLC mobile phase: 0-90% acetonitrile-water (0.1% trifluoroacetic acid)

Peak retention time: 19 minutes (Waters, Alliance 2695, column: Tosoh ODS-100V, UV: 254 nm)

ESIMS (positive) m/z: 735.3, (M+H) (F.W=734.8 for $C_{40}H_{42}N_6O_8$)

(Waters, LCT Premier, column: Tosoh ODS-100V)

[Chem. 23]

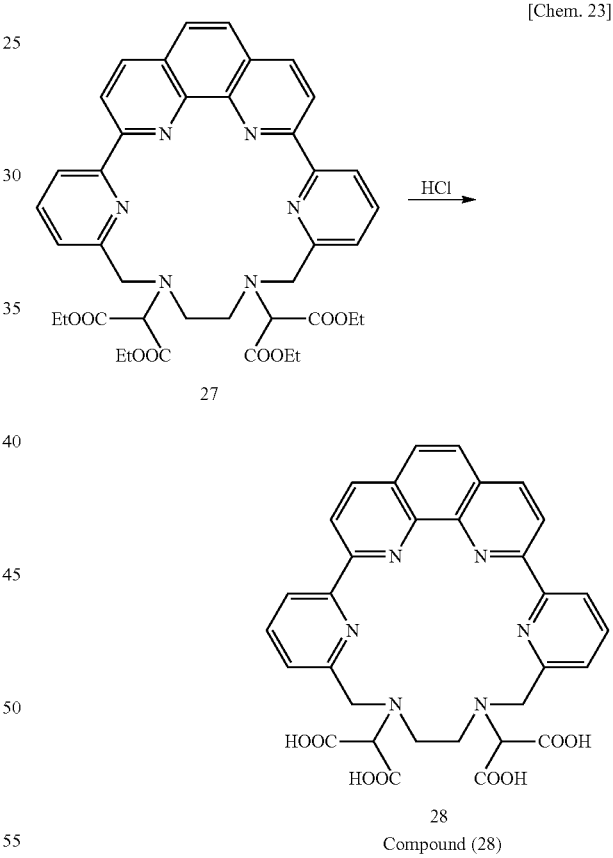

Compound (28)

Under a stream of argon, to compound (27) (34.1 mg), methanol (3 mL) and 12 N hydrochloric acid (0.041 mL) were added. The resulting reaction mixture was stirred and refluxed for 4 hours at 85° C. The reaction mixture was cooled to room temperature, and the reaction mixture was extracted by addition of chloroform (3 mL) and water (3 mL). Moreover, the organic layer was further extracted three times with water (1 mL). The resulting aqueous phase was separated by column chromatography (LH-20/MeOH) to obtain an aqueous solution of the title compound (28).

Production Example 1

1-Methyl-1,10-phenanthrolinium iodide (1)

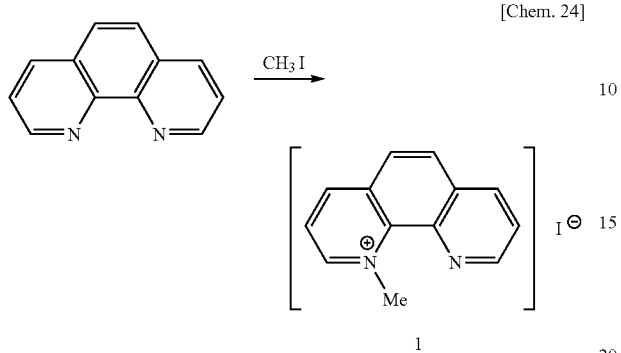

[Chem. 24]

Under a stream of argon, 1,10-phenanthroline (23 g; 127 mmol) was dissolved in nitrobenzene (500 mL). To the reaction mixture, methyl iodide (45.29 g; 319 mmol) was 35° C. for 24 hours. The reaction mixture was cooled in an ice bath, filtered out. The resulting solids were sequentially washed with nitrobenzene, benzene, and ethanol, and evaporated under reduced pressure to give 36 g (yield: 88%) of the title compound (1).
$^1$H NMR (DMSO-$d_6$)d: 5.29 (s, 3H), 8.07 (d, d, J1=8 Hz, J2=4.5 Hz, 1H), 8.43 (d, J=2.5 Hz, 1H), 8.43 (q, J=9 Hz, 2H), 8.81 (d, d, J1=8.5 Hz, J2=1.5 Hz, 1H), 9.32-9.60 (m, 3H)

Production Example 2

1-Methyl-1,10-phenanthrolin-2(1H)-one (2)

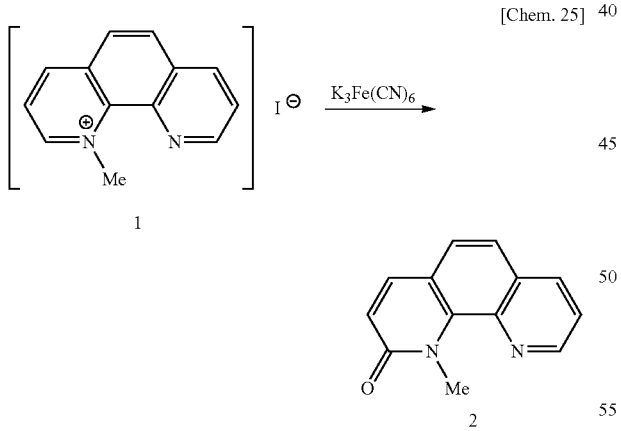

[Chem. 25]

To a stirred aqueous solution of potassium ferricyanide (92.2 g; 280 mmol) (1.12 L), compound (1) (37.6 g; 117 mmol) and an aqueous solution of sodium hydroxide (69.3 g; 1.73 mol) (200 mL) were alternately added in an ice bath (inner temperature of 10 to 15° C.) over 20 minutes. The resulting reaction mixture was stirred at room temperature for 3 hours. Crude crystals which precipitated out were filtered out and dried. The resulting crude crystals were dissolved in toluene (1.1 L) and benzene (450 mL), and insoluble matters were filtrated out. The filtrate was evaporated under reduced pressure, and the resulting residue was washed with isopropyl ether and ethyl acetate, and then dried to give 23.7 g (yield: 75%) of the title compound (2).
$^1$H NMR (DMSO-$d_6$)d: 4.22 (s, 3H), 6.84 d, J=9 Hz, 1H), 7.69 (d, d, J1=8 Hz, J2=2 Hz, 1H), 7.77 (d, J=8 Hz, 1H), 7.82 (d, J=8.5 Hz, 1H), 8.08 (d, J=9.5 Hz, 1H), 8.46 (d, d, J1=8 Hz, J2=2 Hz, 1H), 9.0 (d, d, J1=9.5 Hz, J2=2 Hz, 1H)

Production Example 3

2-Chloro-1,10-phenanthroline (3)

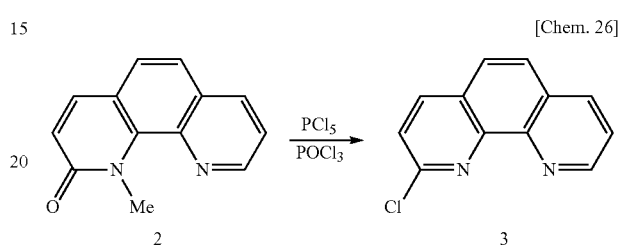

[Chem. 26]

Under a stream of argon, to compound (2) (8 g; 38 mmol), phosphorus oxychloride (72 mL) and phosphorus pentachloride (9.8 g; 47.6 mmol) were added in an ice bath. The resulting reaction mixture was stirred and refluxed for 8 hours, and excess phosphorus oxychloride was removed under reduced pressure. To the resulting reaction concentrate, ice water and concentrated aqueous ammonia were added and the resulting mixture was made alkaline to precipitate crude crystals. The crude crystals were separated by filtration and washed with water, and then dried under reduced pressure to give 6.1 g (yield: 75%) of the title compound (3).
$^1$H NMR (DMSO-$d_6$)d: 7.80-7.88 (m, 2H), 8.07 (s, 2H), 8.54 (d, J=8.5 Hz, 1H), 8.60 (d, J=8.5 Hz, 1H), 9.14 (d, J=7 Hz, 1H)

Production Example 4

9-Chloro-1-methyl-1,10-phenanthrolinium hydrogen sulfate (4)

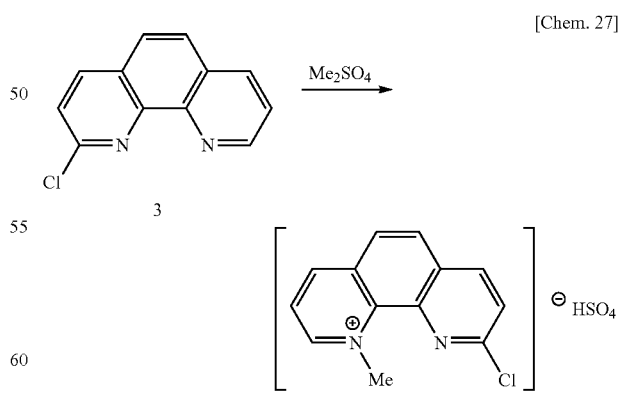

[Chem. 27]

Under a stream of argon, to compound (3) (5.2 g; 24.2 mmol), dimethyl sulfate (22.1 g; 175 mmol) was added at room temperature over 10 minutes. The reaction temperature was raised to 120° C. and the resulting reaction mixture was stirred for 1 hour and then cooled to room temperature. Diethyl ether was added thereto and light brown crude crystals which precipitated out were separated by filtration. The obtained crude crystals were washed with a solution of diethyl ether/ethanol=1/1 to 1/2 and dried under reduced pressure to give 6.17 g of the title compound (4).

$^1$H NMR (DMSO-$d_6$)d: 5.12 (s, 3H), 8.18 (d, J=8.5 Hz, 1H), 8.40-8.50 (m, 3H), 8.88 (d, J=9 Hz, 1H), 9.42 (d, J=9 Hz, 1H), 9.60 (d, J=7 Hz, 1H)

Production Example 5

9-Chloro-1-methyl-1,10-phenanthrolin-2(1H)-one (5)

[Chem. 28]

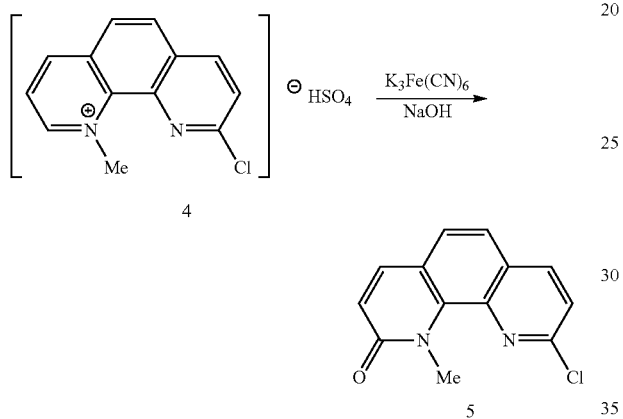

To a stirred aqueous solution of potassium ferricyanide (22.1 g; 673 mmol) (200 mL) in an ice bath, compound (4) (6.17 g; 26.9 mmol) and an aqueous sodium hydroxide (16.14 g; 404 mmol) (110 mL) were alternately added over 20 minutes. The resulting reaction mixture was stirred in an ice bath, and further stirred at room temperature for 3.5 hours. Crude crystals which precipitated out were separated by filtration and dried, and then dissolved in methanol, and subsequently subjected to an activated carbon treatment. Then, a filtrate was concentrated under reduced pressure to give 4.26 g (yield: 72% from compound (3)) of the title compound (5).

$^1$H NMR (DMSO-$d_6$)d: 4.35 (s, 3H), 6.87 (d, J=9 Hz, 1H), 7.76 (d, J=8.5 Hz, 1H), 7.83 (d, J=8.5 Hz, 1H), 7.89 (d, J=8.5 Hz, 1H), 8.09 (d, J=9 Hz, 1H), 8.54 (d, J=9 Hz, 1H)

Production Example 6

2,9-Dichloro-1,10-phenanthroline (6)

[Chem. 29]

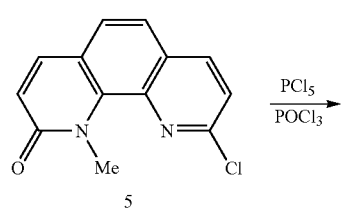

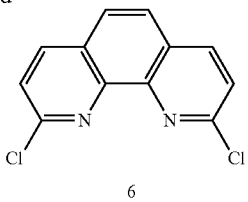

Under a stream of argon, to compound (5) (4.26 g; 17.4 mmol), phosphorus oxy-chloride (39 mL) and phosphorus pentachloride (4.48 g; 21.8 mmol) were added in an ice bath. The resulting reaction mixture was stirred and refluxed for 7 hours, and then evaporated under reduced pressure to remove phosphorus oxychloride. To the resulting residue, ice water and concentrated aqueous ammonia were added and the resulting reaction mixture was made alkaline. The solids which precipitated out were separated by filtration and washed with water, and then dried under reduced pressure to give 4.06 g (yield: 94%) of the title compound (6).

$^1$H NMR (DMSO-$d_6$)d: 7.90 (d, J=8.5 Hz, 1H), 8.12 (s, 2H), 8.63 (d, J=8.5 Hz, 1H) HPLC mobile phase: 20-90% acetonitrile-water (0.1% trifluoroacetic acid) Peak retention time: 13.2 minutes Production Example 7

2-Bromo-1,10-phenanthroline (7)

[Chem. 30]

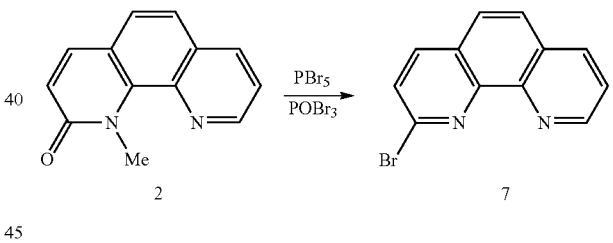

Under a stream of argon, to compound (2) (10 g; 47.6 mmol), phosphorus pentabromide (28 g; 65 mmol) and phosphorus oxybromide (50 g; 174 mmol) were added at room temperature. The reaction temperature was raised to 80° C. and the reaction mixture was stirred for 6 hours. The reaction mixture was cooled in an ice bath, and then poured into ice water. Concentrated aqueous ammonia was added thereto and the resulting mixture was made alkaline. The reaction mixture was extracted with chloroform, and the organic layer thus obtained was washed with water, dried over sodium sulfate, and then evaporated under reduced pressure. The resulting residue was separated and purified by silica gel column chromatography (SiO$_2$, 250 g) (toluene/ethyl acetate=5/1 to 3/1 to 1/1 to ethyl acetate), to give 6.9 g (yield: 94%) of the title compound (7).

$^1$H NMR (CDCl$_3$)d: 7.66 (d, d, J1=8 Hz, J2=4.5 Hz, 1H), 7.76-7.79 (m, 2H), 7.83 (d, J=8.5 Hz, 1H), 8.08 (d, J=8.5 Hz, 1H), 8.26 (d, d, J1=8 Hz, J2=2 Hz, 1H), 9.24 (d, J1=4.5 Hz, J2=2 Hz, 1H)

HPLC mobile phase: 20-90% acetonitrile-water (0.1% trifluoroacetic acid) Peak retention time: 4.2 minutes ESIMS (positive) m/z: 260.9, 258.2 (M+H) (F.W=259.1 for $C_{12}H_7BrN_2$)

Production Example 8

9-Bromo-1-methyl-1,10-phenanthrolinium hydrogen sulfate (8)

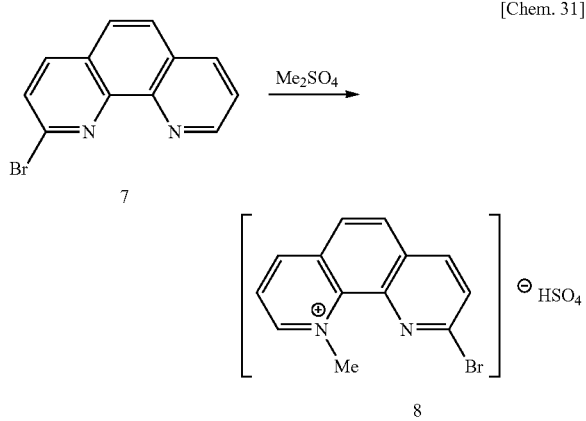

Under a stream of argon, to compound (7) (24.4 g; 94.2 mmol), dimethyl sulfate (77 g; 610 mmol) was added in an ice bath over 20 minutes. The reaction temperature was raised to 120° C. and the resulting reaction mixture was stirred for 1 hour. To the reaction mixture, diethyl ether was added in an ice bath, and solids which precipitated out were separated by filtration. The resulting solids were washed with a mixed solution of diethyl ether/ethanol (1/1 to 1/2) and dried under reduced pressure to give 33.6 g (yield: 96%) of the title compound (8).

$^1$H NMR (DMSO-$d_6$)d: 5.19 (s, 3H), 8.29 (d, J=8.5 Hz, 1H), 8.43-8.50 (m, 3H), 8.77 (d, J=8.5 Hz, 1H), 9.44 (d, J=8.5 Hz, 1H), 9.64 (d, J=6 Hz, 1H) HPLC mobile phase: 20-90% acetonitrile-water (0.1% trifluoroacetic acid) Peak retention time: 5.2 minutes ESIMS (positive) m/z: 274.9, 272.9 (M+H) (F.W=274.14 for $C_{13}H_{10}BrN_2$)

Production Example 9

9-Bromo-1-methyl-1,10-phenanthrolin-2(1H)-one (9)

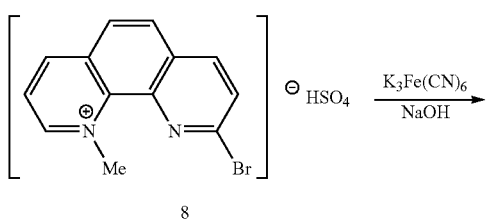

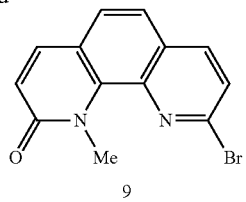

To a stirred aqueous solution of potassium ferricyanide (100 g; 303 mmol) (1.1 L), compound (8) (42.7 g; 115 mmol) and an aqueous sodium hydroxide (76 g; 1.9 mol) (110 mL) were alternately added over 25 minutes in an ice bath (inner temperature of 4 to 6° C.). The resulting mixture was stirred in an ice bath for 1 hour, and further stirred at room temperature for 3.5 hours. Crude crystals which precipitated out were separated by filtration and washed with water, and then dried. The resulting crude crystals were separated and purified by silica gel column chromatography ($SiO_2$ 800 g) (chloroform/methanol=50/1 to 30/1 to 20/1) and dried to give 27.4 g (yield: 82%) of the title compound (9).

$^1$H NMR ($CDCl_3$)d: 4.39 (s, 3H), 6.92 (d, J=9.5 Hz, 1H), 7.54 (d, J=8.5 Hz, 1H), 7.60 (d, J=8.5 Hz, 1H), 7.61 (d, J=8.5 Hz, 1H), 7.77 (d, J=9.5 Hz, 1H), 8.01 (d, J=8.5 Hz, 1H)

HPLC mobile phase: 20-90% acetonitrile-water (0.1% trifluoroacetic acid) Peak retention time: 14.2 minutes ESIMS (positive) m/z: 290.9, 288.2 (M+H) (F.W=289.13 for $C_{13}H_9BrN_2O$)

Production Example 10

2,9-Dibromo-1,10-phenanthroline (10)

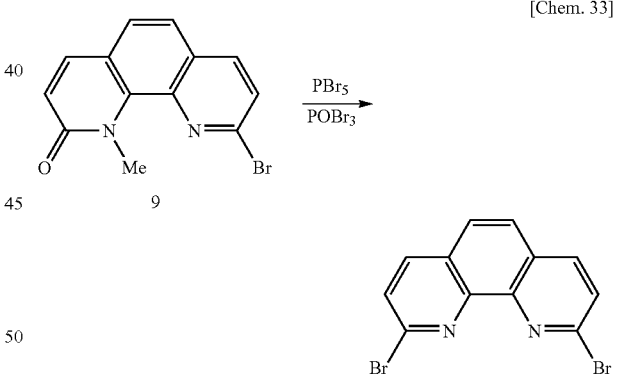

Under a stream of argon, to compound (9) (8.4 g; 29.1 mmol), phosphorus oxybromide (3.25 g; 174 mmol) and phosphorus pentachloride (15.4 g; 35.8 mmol) were added in an ice bath. The reaction temperature was raised to 65 to 75° C., and the resulting reaction mixture was stirred for 5.5 hours. The reaction mixture was cooled in an ice bath and evaporated under reduced pressure. Excess phosphorus oxybromide was removed and the resulting reaction concentrate was poured into ice water, and was made alkaline with concentrated aqueous ammonia. While solids which precipitated out were separated by filtration, they were washed with water to give crude title compound (10). The crude compound (10) was dried, and separated and purified by silica gel column chromatography (SiO$_2$ 300 g) (CHCl$_3$/methanol=50/1 to 40/1 to 30/1) to give 8 g (yield: 81%) of the title compound (10).

$^1$H NMR (CDCl$_3$)d: 8.02 (d, J=8.5 Hz, 2H), 8.12 (s, 2H), 8.51 (d, J=8.5 Hz, 2H) HPLC mobile phase: 20-90% acetonitrile-water (0.1% trifluoroacetic acid) Peak retention time: 16 minutes ESIMS (positive) m/z: 340.8, 338.8, 336.8 (M+H) (F.W=338.00 for C$_{12}$H$_6$Br$_2$N$_2$)

Production Example 11

2-Bromo-6-((methoxymethyloxy)methyl)pyridine (11)

[Chem. 34]

Under a stream of argon, (6-bromopyridine-2-yl)methanol (10 g; 53.2 mmol) was dissolved in methylene chloride (50 mL). Diisopropylethylamine (9.6 g; 74.5 mmol) and chloromethyl methyl ether (5.35 g; 66.5 mmol) were added to the reaction mixture in an ice bath, and further, the reaction mixture was stirred at room temperature for 17 hours. The reaction solution was poured into ice water and extracted with chloroform. The organic layer was washed with water, dried over sodium sulfate, and then evaporated under reduced pressure. The resulting residue was separated and purified by silica gel column chromatography (SiO$_2$, 200 g) (toluene/ethyl acetate=10/1) to give 12.15 g (yield: 98%) of the title compound (11).

$^1$H NMR (CDCl$_3$)d: 3.42 (s, 3H), 4.69 (s, 2H), 4.77 (s, 2H), 7.38-7.44 (m, 2H), 7.56 (t, J=7.5 Hz, 1H)

Production Example 12

2-((Methoxymethyloxy)methyl)-6-(tributylstannyl)pyridine (12)

[Chem. 35]

Under a stream of argon, compound (11) (24.7 g; 106 mmol) was dissolved in anhydrous tetrahydrofuran (270 mL), and 1.54M n-butyllithium hexane solution was added dropwise thereto over 50 minutes at −65 to −70° C. The resulting reaction mixture was stirred at −65 to −70° C. for 1 hour. To the reaction mixture, tetrahydrofuran solution of 40 g (122 mmol) of tributyltin chloride (100 mL) was added dropwise over 30 minutes. While gradually raising the temperature of the reaction solution (to −20° C.), the reaction mixture was stirred at −20° C. for 20 hours. To the reaction mixture, water (250 mL) was added, and the resulting mixture was extracted with diethyl ether three times. The organic layer was dried over magnesium sulfate and evaporated under reduced pressure to give 58 g of the crude title compound (12). The obtained compound was used in the next step without further purifying.

INDUSTRIAL APPLICABILITY

The rare earth metal complex having a phenanthroline compound as a ligand of the present invention is useful as an analytical marker that utilizes emission of light.

The invention claimed is:

1. A rare earth metal complex represented by the following formula (I):

(I)

wherein:
M represents a divalent or trivalent rare earth metal ion,
R$_3$ and R$_4$ are the same as or different from each other and each independently represents (1) a hydrogen atom, (2) a C$_{1-6}$ alkyl group, (3) a C$_{3-8}$ cycloalkyl group, (4) a C$_{2-6}$ alkenyl group, (5) a C$_{2-6}$ alkynyl group, (6) a C$_{6-14}$ aryl group, (7) a C$_{7-20}$ aralkyl group, or (8) a negative charge,
X$_1$ and X$_2$ are the same as or different from each other and each independently represents the following structure:

—(CH$_2$)$_m$—   or   —(CH$_2$)$_{m-1}$CH—
                                          |
                                          COOR$_5$ wherein:
m represents an integer of 1 to 6, and R$_5$ represents (1) a hydrogen atom, (2) a C$_{1-6}$ alkyl group, (3) a C$_{3-8}$ cycloalkyl group, (4) a C$_{2-6}$ alkenyl group, (5) a C$_{2-6}$ alkynyl group, (6) a C$_{6-14}$ aryl group, (7) a C$_{7-20}$ aralkyl group, or (8) a negative charge, and
Y represents an anion or is not present.

2. The rare earth metal complex according to claim 1, wherein each of R$_3$ and R$_4$ independently represents a hydrogen atom or a negative charge.

3. The rare earth metal complex according to claim 1, wherein the rare earth metal is europium.

4. A fluorescent labeling agent containing the rare earth metal complex according to claim 1.

5. The rare earth metal complex according to claim 1, wherein the rare earth metal is terbium.

6. The rare earth metal complex according to claim 1, wherein the rare earth metal is lanthanum.

7. The rare earth metal complex according to claim 1, wherein the rare earth metal is cerium.

8. The rare earth metal complex according to claim 1, wherein the rare earth metal is praseodymium.

9. The rare earth metal complex according to claim 1, wherein the rare earth metal is neodymium.

10. The rare earth metal complex according to claim 1, wherein the rare earth metal is promethium.

11. The rare earth metal complex according to claim 1, wherein the rare earth metal is samarium.

12. The rare earth metal complex according to claim 1, wherein the rare earth metal is gadolinium.

13. The rare earth metal complex according to claim 1, wherein the rare earth metal is dysprosium.

14. The rare earth metal complex according to claim 1, wherein the rare earth metal is holmium.

15. The rare earth metal complex according to claim 1, wherein the rare earth metal is erbium.

16. The rare earth metal complex according to claim 1, wherein the rare earth metal is thulium.

17. The rare earth metal complex according to claim 1, wherein the rare earth metal is ytterbium.

18. The rare earth metal complex according to claim 1, wherein the rare earth metal is lutetium.

19. The rare earth metal complex according to claim 1, wherein the rare earth metal is scandium.

20. The rare earth metal complex according to claim 1, wherein the rare earth metal is yttrium.

* * * * *